(12) United States Patent
Bullock

(10) Patent No.: US 12,102,519 B1
(45) Date of Patent: Oct. 1, 2024

(54) METHODS AND TECHNIQUES FOR TREATING FACIAL ASSYMETRY BY ADMINISTERING DERMAL INJECTIONS TO PATIENTS BASED UPON GESTATIONAL PATTERNS

(71) Applicant: Bobbi Annette Bullock, Boise, ID (US)

(72) Inventor: Bobbi Annette Bullock, Boise, ID (US)

(73) Assignee: Innovation LLC, Boise, ID (US)

( * ) Notice: Subject to any disclaimer, the term of this patent is extended or adjusted under 35 U.S.C. 154(b) by 0 days.

(21) Appl. No.: 18/383,582

(22) Filed: Oct. 25, 2023

(51) Int. Cl.
*A61F 2/00* (2006.01)
*A61B 17/00* (2006.01)

(52) U.S. Cl.
CPC ............ *A61F 2/0059* (2013.01); *A61B 17/00* (2013.01); *A61B 2017/00747* (2013.01)

(58) Field of Classification Search
CPC ......... A61F 2/0059; A61B 2017/00747; A61B 17/00
See application file for complete search history.

(56) References Cited

PUBLICATIONS

Maio, M., "MD Codes TM: A Methodological Approach to Facial Aethetic Treatment with Injectable Hyaluronic Acid Fillers," Aeth Plastic Surger (2021) 45:690-709.

Allergan Medical Institute, MD Codes TM, Paradigm Tour 2020, National Virtual Series Program Episode 1 Workbook: Unlocking the MD Codes TM, 21 pages.

Allergan Medical Institute, MD Codes TM, Paradigm Tour 2020, National Virtual Series Program Episode 3 Workbook: Precision in Dynamics with the MD DYNA Codes TM, 17 pages.

Allergan Medical Institute, The MD Codes TM: Enhancing Your Treatment Approach with Juvederm R Voluma TM XC, One Filler Uniquely Designed for Two Areas of the Face, 8 pages.

Maio, M., "MD Codes TM: A Methodological Approach to Facial Aethetic Treatment with Injectable Hyaluronic Acid Fillers-Correction," Aeth Plastic Surger (2021) 45:838-843.

*Primary Examiner* — Deanna K Hall
(74) *Attorney, Agent, or Firm* — Lowe Graham Jones PLLC; Ellen M. Bierman

(57) ABSTRACT

Embodiments described herein provide enhanced methods, techniques, and methods of treatment for consistently correcting facial asymmetries caused by gestational position of a fetus in utero using an improved method of treatment based upon facial asymmetry grading. With SSM, the patient is evaluated to determine whether their facial asymmetries are a result of FLT; and assuming so, a determination is made as to the severity of the asymmetries based upon the asymmetry severity scale guide. Based upon the determined severity and type of asymmetry, the injector performs an SSM plan that consistently corrects such asymmetries by injecting more filler to the more contoured side of the face as opposed to the heavier side, and in consistent amounts and to certain locations.

26 Claims, 22 Drawing Sheets
(18 of 22 Drawing Sheet(s) Filed in Color)

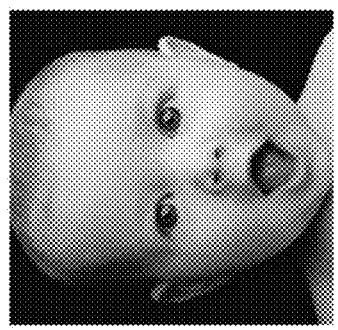
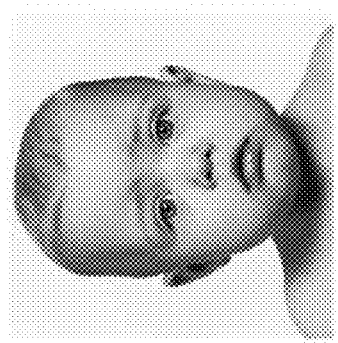
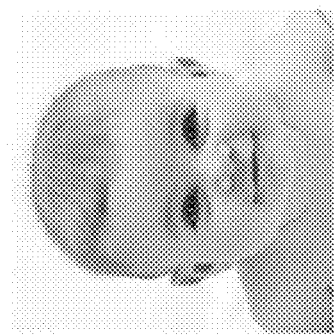
Fig. 4

Asymmetry Severity Scale Guide (ASSG)

| ASSG Grade | Description | FLT position | SS (Method of Treatment) |
|---|---|---|---|
| SS: Grade 1 (SS-G1) MILD | This is approximately 4% of the population (outlier). This asymmetry is not easily recognized by the average observer. These are typically very beautiful people or those with a very thin and narrow or a very round face or those with undistinguished or undefined contour (flat bones). | These people gestated breech or were born premature (<38 weeks) or by cesarean section due to other reasons than failure to descend in the birth canal. | Approximately 15% more filler collectively used on more contoured side of the face (L side if LOA; R side if ROA). Range of filler applied is 10-20%, with 15% plus/minus being typical. Approximately 10% more filler applied to the light reflective area of the heavier side (R side if LOA; L side if ROA) |
| SS: Grade 2 (SS-G2) MODERATE | This is approximately 93% of the general population. Most people are unaware they have facial asymmetry, and are typically surprised when it is identified, or if aware, they are certain their asymmetry is caused from a traumatic facial injury, sleeping on their face or solar damage. | Those who gestated in the LOA or ROA position. (When ROA is considered counter position and the Grade is SS-CP-G1 or G2). Birth could be vaginal or cesarean. | Approximately 25% more filler collectively used on the more contoured side of the face (L side if LOA; R side if ROA). Range of filler applied is 21-30%, with 25% plus/minus being typical. Approximately 10% more filler applied to the light reflective area of the heavier side (R side if LOA; L side if ROA) |
| SS: Grade 3 (SS-G3) SEVERE | This is approximately 2% of the population (outlier). The person is aware of their asymmetries. | This population in utero had low amniotic fluid, or a troublesome pregnancy such as advanced maternal age, smoking, intrauterine growth restriction, etc. They may additionally have a genetic, pregnancy or acquired syndrome unrelated to the FLT causing asymmetries. The patient would be aware of these conditions and could be queried. | Correction is case by case and there is no consistent FLT due to malformations. The correction is not currently considered part of SSM. |

Fig. 7

KEY: Injection Sequence

Stand alone injections or in any order:
- Z1, Z2, Z4

Sequenced zones:
- Z3 after Z2
- Z5 after Z2,Z3, Z4
- Z6 after Z2, Z3, Z4, Z5

ASSG SS-G2 Volumes:

Total 16 syringes for full correction:
Collectively needs ~25% more filler volume on L side with ~10% more filler on the superior R LRA than on the L LRA

- 9cc on Left side of face
- 7cc on Right side of face.

Asymmetry Severity Scale Guide (ASSG) Grade 1 (G1) "Mild"
Type A (contour > juicy)
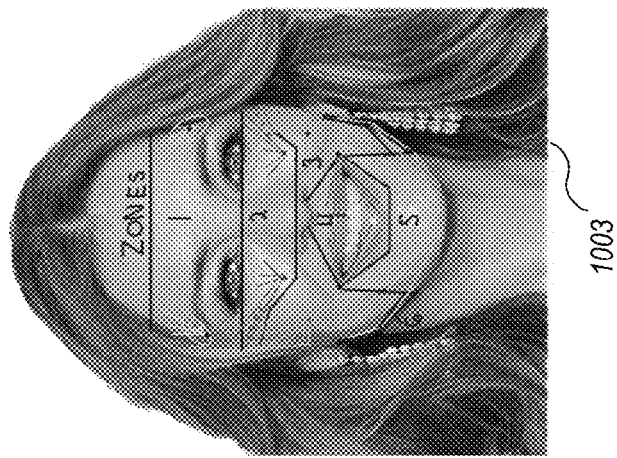
1003
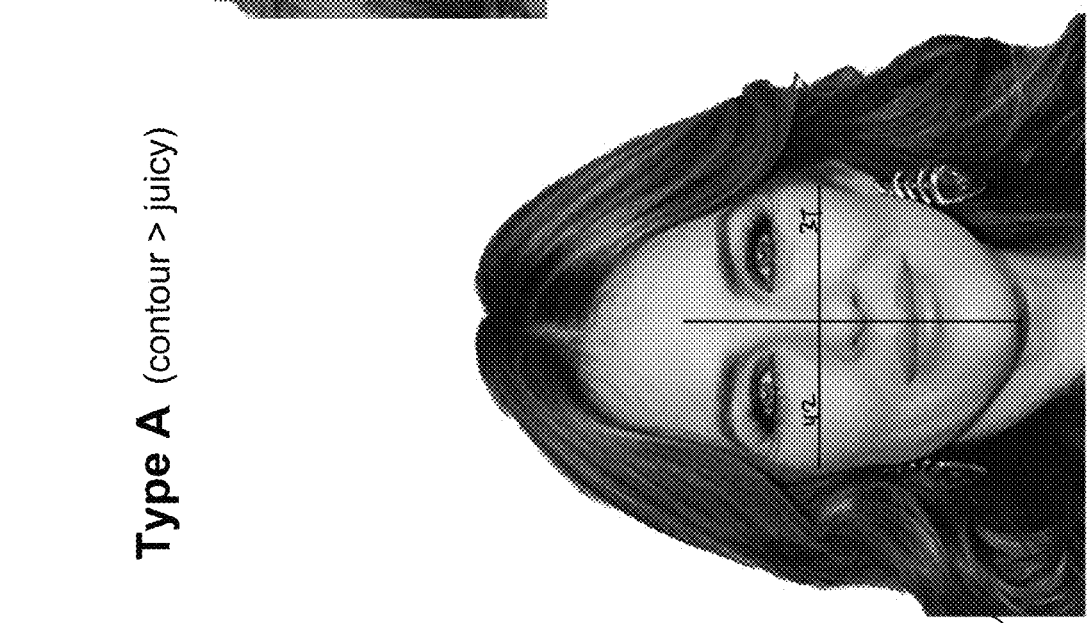
1001
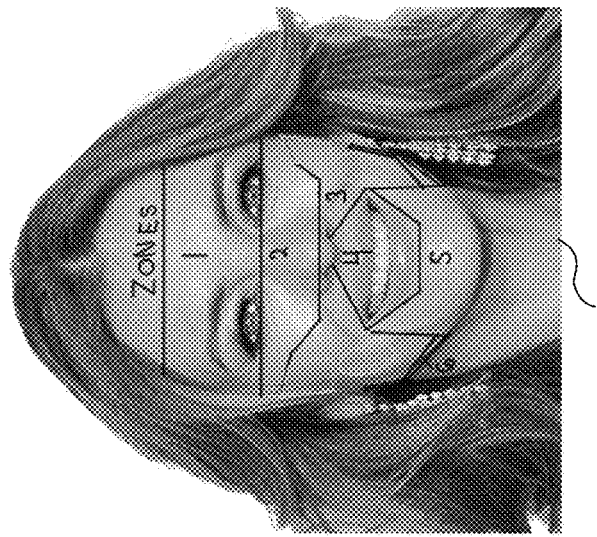
1002
*Fig. 10*

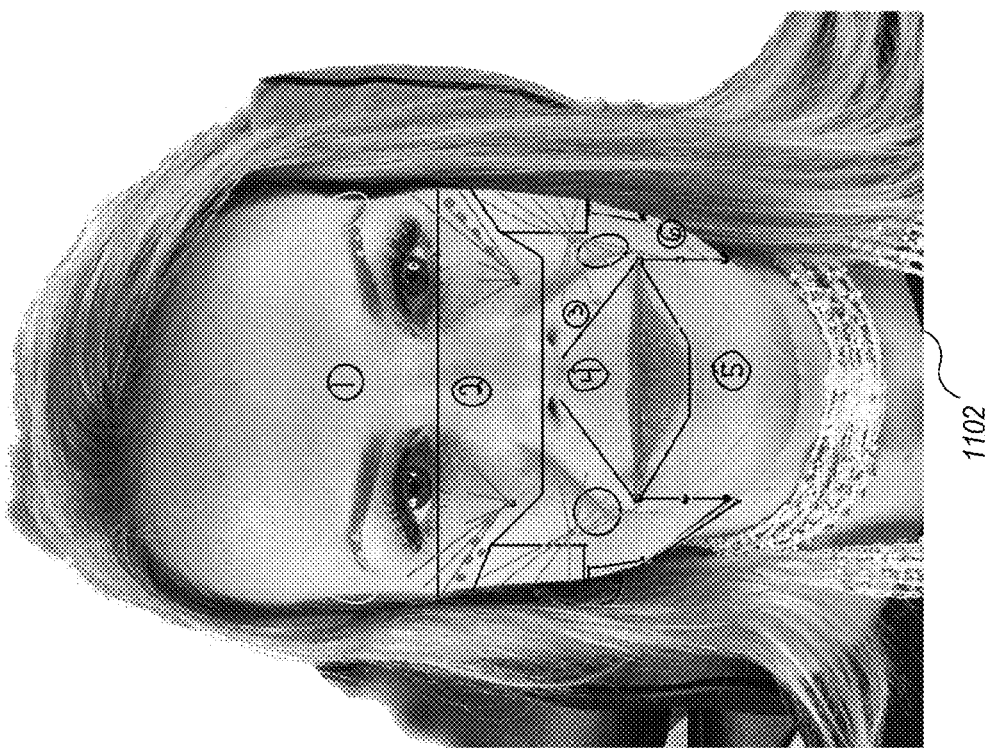
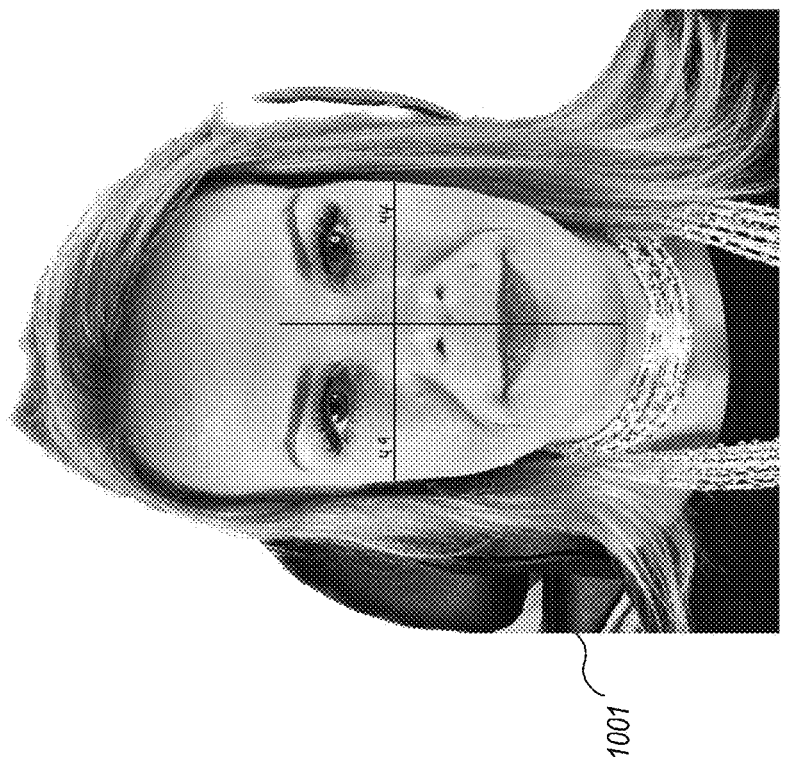
Fig. 11

Asymmetry Severity Scale Guide (ASSG) Counter Position
Example for Moderate – SS-CP-G2
ROA Gestation
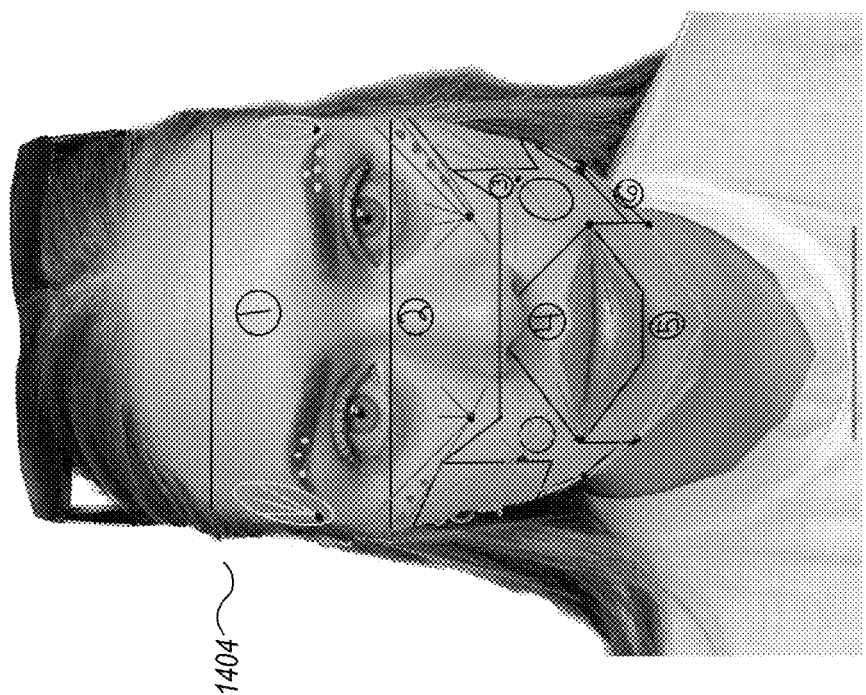
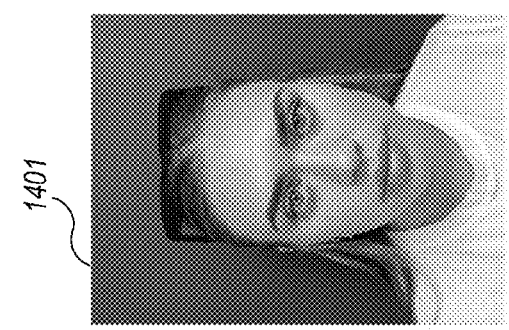
Fig. 14

Fig. 16 Injecting Filler Using SSM to reduce Asymmetry (SS-G2)

Lip and Mouth Asymmetry Corrected SS-G2

KEY: Total Correction:   1cc with 0.15cc more on the L side
- SS-Lip-G1-10% more filler on the L lip and mouth
- SS-Lip-G2-15% more filler on the L lip and mouth
- SS-Lip-CB- Follow the ASSG, and place more on the R lip and mouth

US 12,102,519 B1

METHODS AND TECHNIQUES FOR TREATING FACIAL ASSYMETRY BY ADMINISTERING DERMAL INJECTIONS TO PATIENTS BASED UPON GESTATIONAL PATTERNS

TECHNICAL FIELD

The present disclosure relates to methods, techniques, and systems for detecting and correcting facial asymmetry caused during fetal gestation in utero and, in particular, to methods, techniques, and systems for predicting, planning, and consistently administering dermal injections uniquely to each side of a patient's face in amounts and locations corresponding to severity and type of gestational facial asymmetry.

BACKGROUND

Non-surgical cosmetic procedures are often used to correct and enhance features of patients. For example, medical professionals (including "aestheticians" or "estheticians") can apply various kinds of dermal fillers to decrease visible signs of aging due to volume loss. As people age their facial tissues become thinner, the lines near their nose and mouth become accentuated and their cheeks start looking deflated, flat, and hollow. Dermal fillers can be injected by medical professionals to replace lost volume, for example, to help smooth wrinkles, plump lips, and restore a more youthful appearance. Most dermal fillers are gel-like substances that are injected beneath the skin to restore lost volume, smooth lines and soften creases, or enhance facial contours. According to the American Board of Cosmetic Surgery, "[m]ore than 1 million men and women annually choose this popular facial rejuvenation treatment, which can be a cost-effective way to look younger without surgery or downtime." Common dermal fillers include Hyaluronic Acid (HA), Calcium Hydroxylapatite (CaHA), Poly-L-Lactic Acide, Polmethylmethacrylate (PMMA), and Autologous fat injections (facial fat grating). A multitude of different dermal filler products are available from many different pharmaceutical companies, e.g., BOTOX® and JUVÉDERM® by Allergan (AbbVie). (For further information, see "https://www.americanboardcosmeticsurgery.org/procedure-learning-center/non-surgical/injectable-fillers-guide/".)

Dermal fillers also can be used to correct facial asymmetry, i.e., differences from one side of the face to the other as to various features and appearance. Asymmetry is difficult to detect and define for patients and for injectors and other medical professionals because most people don't know they have facial asymmetry and cannot see it in others. It is also difficult to define because we have two eyes, one nose, and one mouth. Further, the face is constantly moving through animation, and we typically look at others at an angle—the straightforward stare is reserved for intimate moments and for those with whom we are angry.

Furthermore, a bit of asymmetry creates something interesting to look at as long as it does not deviate too much from acceptable norms (which may be culturally influenced) and is not considered a birth defect. Most of these asymmetries can only be seen in still, flat faced photos once it is identified. Facial asymmetry can affect bone structure and soft tissue, muscles, nerves and structures during animation. For example, a mouth at rest can appear symmetrical, but upon animation, it can pull to one side.

Facial asymmetry is typically thought by injectors, medical providers, and patients to be caused by a difficult birth delivery such as with forceps, a facial trauma from youth or adulthood, sleeping on one side of our face, or UV light repetitively shone on the driver's side of the car. Most patients are not even aware that they have facial asymmetry, and no one thinks they were born that way—unless they are clear that they have a birth defect causing certain facial features.

BRIEF DESCRIPTION OF THE DRAWINGS

The patent or application file contains at least one drawing executed in color. Copies of this patent or patent application publication with color drawings will be provided by the Office upon request and payment of any necessary fee.

FIG. 4 illustrates several pictures of infants that demonstrate this consistent facial asymmetry outcomes.

FIG. 7 illustrates the Symmetry Solutions Method of Treatment Asymmetry Severity Scale Guide which provides guidelines for grading and methods of correction.

FIG. 10 illustrates annotated photos of a Type A SSM Grade 1 (SS-G1) mild level of asymmetry.

FIG. 11 illustrates annotated photos of a Type B SSM Grade 1 (SS-G1) mild level of asymmetry.

FIG. 14 illustrates annotated photos of a SSM Grade 2 (SS-G2) moderate level of asymmetry for an individual having a counter position fetal lie.

DETAILED DESCRIPTION

Figure 1:
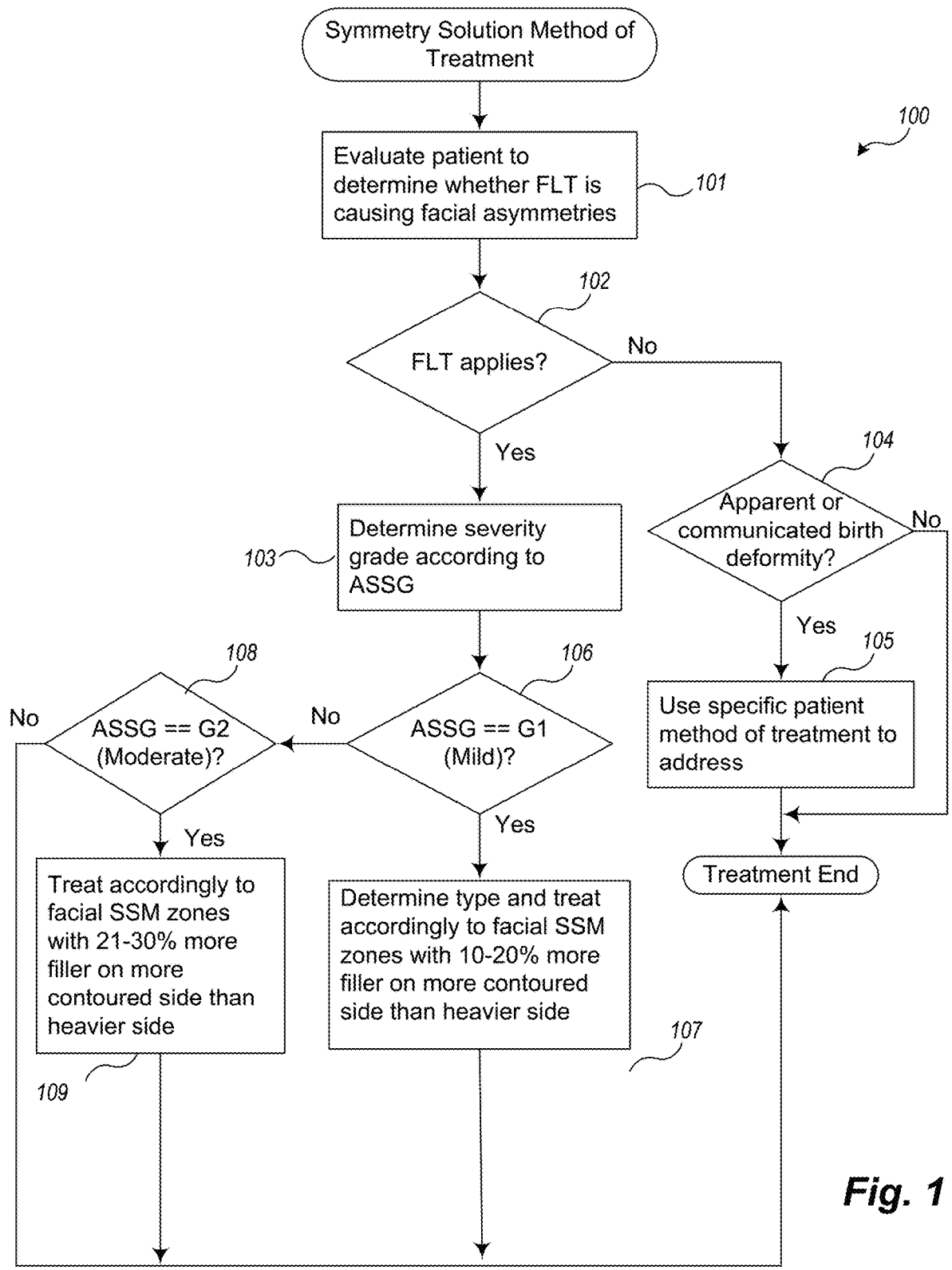
FIG. 1 is an overview of the Symmetry Solutions Method of Treatment used to address facial asymmetries caused by Fetal Lie Theory.

Embodiments described herein provide enhanced methods, techniques, and methods of treatment for consistently correcting facial asymmetries caused by gestational position of a fetus in utero using an improved method of treatment based upon facial asymmetry grading. Examples of using the Symmetry Solutions Method of Treatment ("SSM") to consistently correct asymmetry caused by fetal lie position through dermal injections are provided herein. The methodology embraced by the treatment plans described and exemplified herein are based upon a recognition and discovery, contrary to traditional thought, that a fetus' position during pregnancy consistently results in predictable facial asymmetry aspects and that asymmetry is not typically caused by a difficult birth delivery, a facial trauma, sleeping, or UV light as previously thought. This discovery and theory is referred to herein as the Fetal Lie Theory (or "FLT").

According to FLT, a baby's position during $3^{rd}$ trimester of gestation (i.e., fetal lie position) directly influences the development of facial characteristics such as bone structure and the amount of fatty tissue in certain areas. From FLT, one can learn to detect and expect certain asymmetries in most faces. As a result, injectors can predictably and consistently correct asymmetry of the brow, eye, mouth, cheek, chin and jaw with injectable fillers if the Symmetry Solutions Method of Treatment is properly applied. SSM allows injectors to understand where to place filler to lift and contour heavier, less attractive facial structures and to equalize the more skeletonized and contoured facial features to create symmetry and balance. SSM is based on an asymmetry severity scale guide ("ASSG") developed as a result of understanding the role of FLT in influencing facial asymmetries.

In overview, according to SSM, the patient is evaluated to determine whether their facial asymmetries are a result of FLT. Assuming so, a determination is made as to the severity of the asymmetries based upon the asymmetry severity scale guide. Based upon the determined severity and type of asymmetry, the injector performs a method of treatment (the SSM) that consistently corrects such asymmetries by injecting more filler to the more contoured side of the face as opposed to the heavier side, and more filler to the superior, posterior, and lateral zygoma (the light reflection area of the heavier side), in consistent amounts and to certain locations.

Injecting dermal fillers differently to different sides of the face and injecting more filler to the more contoured side and to the light reflective area of the heavier side is directly contradictory to known and commonly practiced procedures today. Prior to the development of SSM, facial asymmetry has been commonly addressed by injectors (e.g., medical professionals) in an ad-hoc fashion in which the injector guesses where to place dermal filler and in what amounts. Injectors often are taught that symmetry is not achievable do to impossibility, or desirable, as complete symmetry would look unnatural. Therefore, dermal filler should be applied equally (in the same amounts) to both hemi-faces. For further background, see, for example, de Maio, MD Codes™: *A Methodological Approach to Facial Aesthetic Treatment with Injectable Hyaluronic Acid Fillers*, Aesth. Plast. Surg. (2021) 45:690-709. Often injectors are coached to not chase asymmetry because, although very talented injectors can achieve an approximation of symmetry, they cannot articulate or systemize a process for duplication. Thus, the existing thought process of injector leaders is that asymmetry is random and thus doesn't lend itself to a consistent "cure."

FIG. 1 is an overview of the Symmetry Solutions Method of Treatment used to address facial asymmetries caused by Fetal Lie Theory. The SSM comprises a series of steps 100 performed by an injector to consistently correct for asymmetries caused by FLT. According to the first step of SSM (101), the injector evaluates the face of a patient to determine whether the patient suffers from facial asymmetry caused by fetal lie position during gestation that is treatable in accordance with an asymmetry severity scale guide ("ASSG"). In step 102, if FLT is applicable, then the method of treatment continues with step 103, otherwise proceeds to step 104 determine if a birth deformity is the cause of observed asymmetry. If in step 104, the injector determines that a birth defect is primarily responsible for observed asymmetries, then the injector continues in step 105 to apply a patient centric method of injection unique to that patient and the defect and the method of treatment steps are complete. There are several ways an injector might determine that a birth defect is at play, including from patient histories, interviews with the patient, and well-known observable defects (such as Elephantiasis).

In step 103, when it is determined that FLT applies (and is responsible for several predictable facial asymmetries), then in step 106 the injector determines the level of severity of asymmetries using the ASSG. If the injector determines that the severity of the asymmetries is a mild asymmetry (a grade 1 or G1 severity), then the injector proceeds to step 107 to apply the method of treatment for G1 severity, otherwise continues in step 108. For treating G1 severity, the injector applies 10-20% more dermal filler collectively to all facial zones (described below) on the more contoured side of the face than to all facial zones on the heavier side of the face, in terms of total dermal filler applied to each side. For example, if 7 cc is applied on the heavier facial side, then 8 cc, or approximately 15% more, is applied on the more contoured side. In some example treatments, for G1 severity patients, the injector typically applies approximately (+/−) 15% more dermal filler on the contoured side than the on the heavier side of the face. Additionally, in some example treatments, in contradiction to logic, the injector injects more dermal filler to the injection zone encompassing the superior, posterior, and lateral (not medial) portion of the zygoma (the light reflection area or "LRA") on the heavier side of the face than to the same area on the contoured side of the face. In some example treatments, the injector typically applies approximately (+/−) 10% more filler to the light refection area on the heavier side of the face than to the light reflective area on the more contoured side. The method of treatment then ends.

In step 108, the injector determines whether the severity grade of the asymmetries is a moderate asymmetry (a grade 2 or G2 severity. If not, the method of treatment ends. Otherwise, in step 109, for treating G2 severity, the injector applies 21-30% more dermal filler to collectively to all facial zones on the contoured side of the face than to all facial zones on the heavier side of the face, in terms of total dermal filler applied to each side. For example, if 4 cc is applied on the heavier facial side, then 5 cc, or approximately 25% more, is applied on the more contoured side. In some example treatments, for G2 severity patients, the injector typically applies approximately (+/−) 25% more dermal filler on the contoured side than the on the heavier side of the face. Similar to the technique performed for G1 severity, in contradiction to logic, the injector typically applies approximately (+/−) 10% more filler to the light refection area on the heavier side of the face than to the light reflective area on the more contoured side. The method of treatment then ends.

According to SSM, for most consistent results in reducing asymmetry, the face is divided into 6 zones, described further below, and dermal injections are made in a particularized sequence. There are several special locations where particularized treatment is dictated by the new SSM. For example, particularized injections made to a cheek rectangle and cheek circle (the preauricular fossa and the area medial to the masseter) on the more contoured side and injections made to the light reflective area on the heavier side are used to better correct for asymmetry according to the SSM. Collectively, correcting asymmetry in this fashion will blend in the more contoured side reducing skeletonization while tightening and pulling the heavier side laterally thereby reducing the appearance of jowling.

As mentioned in the overview of the Symmetry Solutions Method of Treatment, the injector first evaluates the face of a patient to determine whether the patient suffers from facial asymmetry caused by fetal lie position during gestation that is treatable in accordance with an asymmetry severity scale guide ("ASSG").

Fetal Lie Theory is based upon observations and hypotheses that fetal bone development and formation—and hence bone structure of facial features—is influenced by fetal position during pregnancy. Generally, osteogenesis and ossification describe the bone formation process. During the third month after conception, the osteoblasts change into a periosteum. Osteoblasts penetrate the disintegrating cartilage and replace it with spongy bone. This forms a primary ossification center. Ossification continues from this center toward the ends of the bones.

Figure 2:
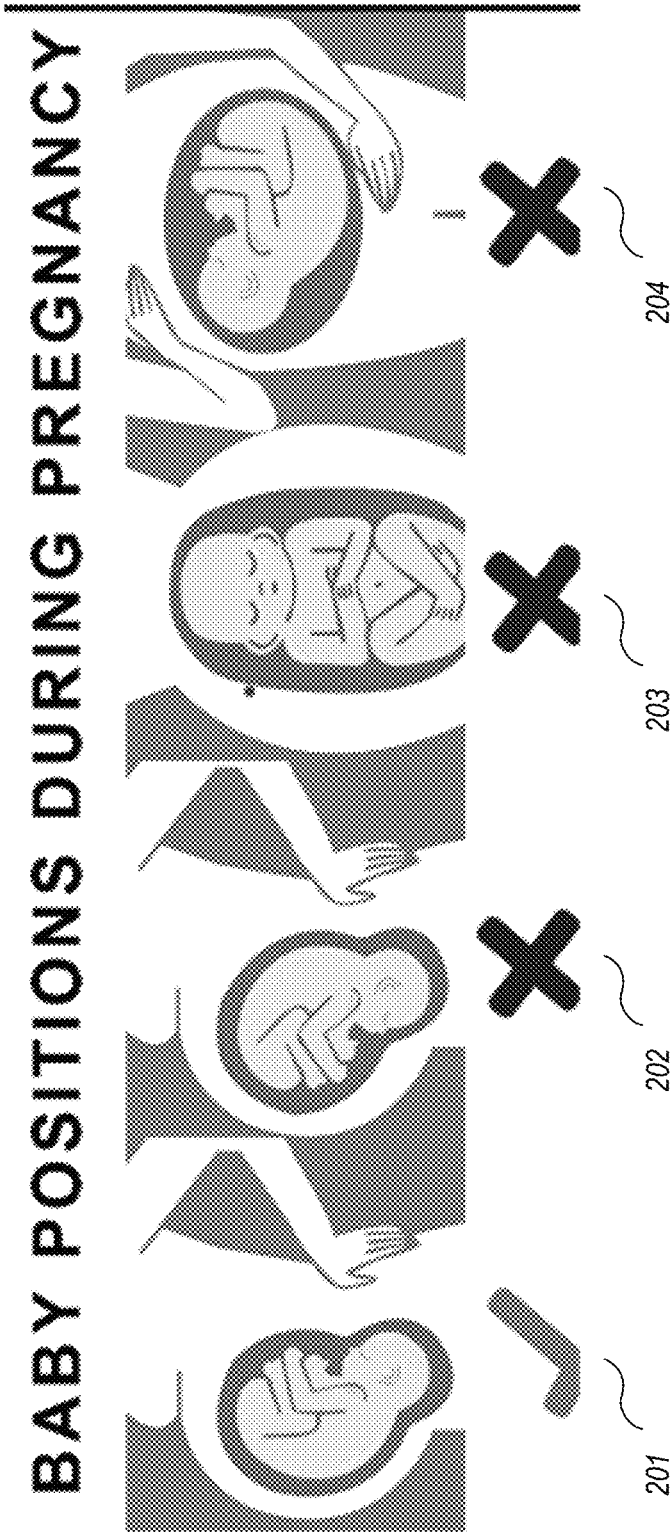
FIG. 2 illustrates the different positions for a fetus at birth.

Before the fetus is born, it is generally positioned for birth. FIG. 2 illustrates the different positions for a fetus at birth. Position 201 is termed Left Occiput Anterior ("LOA"); position 202 is termed Right Occiput Anterior ("ROA"); position 203 is termed "breech" and typically results in a Cesarian section delivery; and position 204 is termed "transverse" and also typically results in a Cesarian section.

Figure 3:
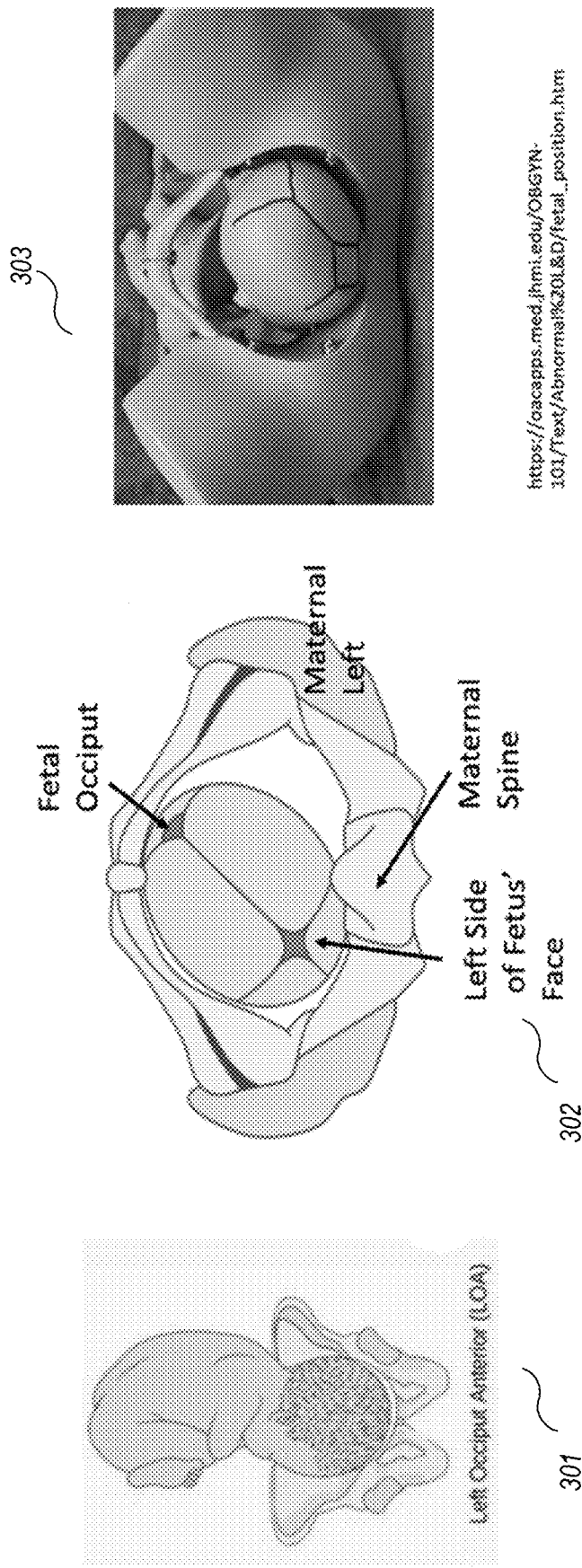
FIG. 3 illustrates diagrams of the LOA position for a fetus.

The most common position for a fetus is the Left Occiput Anterior (LOA) position as it facilitates the easiest fetal position for a natural spontaneous vaginal delivery. FIG. 3 illustrates diagrams of the LOA position for a fetus. Diagrams 301-303 show the fetus lying head down in the uterus, with the left side of the face pressing against the maternal spine and sacrum. In other words, the fetal occiput (back of head) is directed towards the mother's left, anterior side. While in LOA, the left side of the fetal face presses against the maternal spine and pelvis, while the right side does not. The LOA positioning of the fetus occurs around the 34-36 week gestation range and is the most consistent fetal lie. This late gestation period is when the facial bones develop to become the most fixed prior to birth.

Accordingly, we have deduced that, when babies are in this LOA fetal lie position during the late gestation period when the facial bones become the most fixed because their facial bones are finishing ossification, we can predict that the birthed baby will have certain consistent asymmetrical features that result directly from fetal lie position. In particular, we have noted that The left ("L") side of the human face is smaller and more contoured;

The LOA position puts gentle, but consistent pressure on the left, fetal hemi-face against the maternal spine and pelvis, shifting the bones of the jaw and cheek superiorly and laterally;

This pressure decreases the subcutaneous ("SQ," e.g., fatty) tissue on the L side, therefore revealing more contour or a lift;

The right ("R") side of the face is positioned away from the maternal spine, and the fetus' bones and fat are cushioned in amniotic fluid without unusual pressure—and thus are less contoured and fuller (sometimes referred to herein as more "juicy").

FIG. 4 illustrates several pictures of infants that demonstrate this consistent facial asymmetry outcomes. Namely, even when very young, the left side of the infant's face is smaller (however slight) and more contoured, and the right side of the face has more subcutaneous tissue (is fuller) and is less contoured than the left side of the face. This contradicts well established beliefs that asymmetry is likely the result of a facial trauma, side sleeping, or UV light.

In contrast to the LOA positioned fetus, a gestating fetus in the breech position (head up—see position 203 in FIG. 2) would have no difference in pressure on their face, and they would have the most symmetrical faces. Breech presentation occurs in only 3-4% of all the deliveries. As well, those babies with a difficult delivery from mal-positioning such as Right Occiput Posterior (ROA), would have the opposite outcome from the LOA positioned fetuses, namely that the L side of the face would be heavier, and the R side more contoured.

Figure 5:
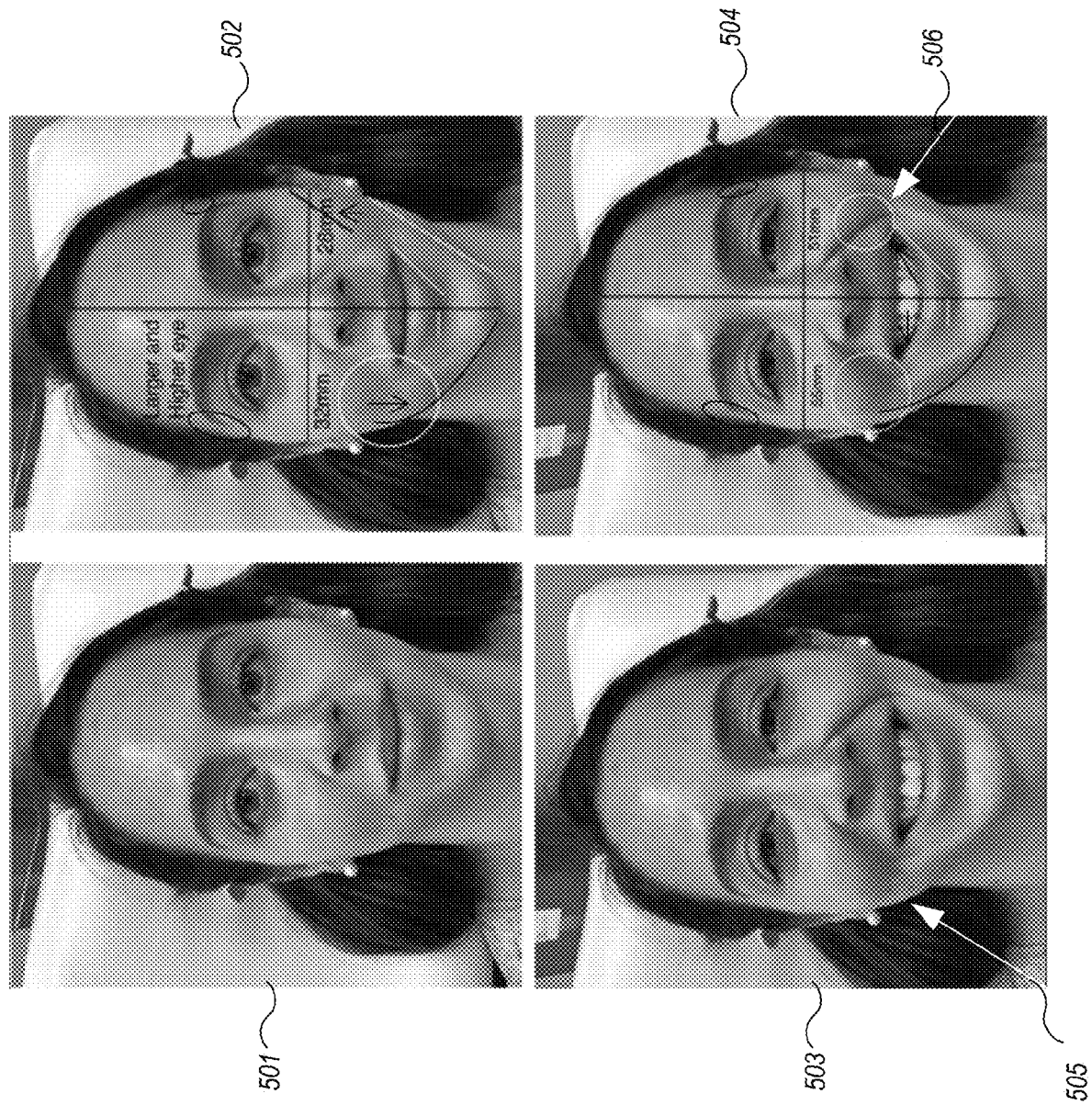
FIG. 5 shows annotated photos of a human face containing facial asymmetries.

In particular, the Fetal Lie Theory (FLT) allows medical providers to ascertain and anticipate that certain asymmetrical facial features are a result of DNA or embryology and that other facial feature asymmetry is a predictable occurrence and thus can be treated predictably and consistently. FIG. 5 shows annotated photos of a human face containing facial asymmetries. Annotated photos 501 and 502 illustrate her face at rest. Annotated photos 503 and 504 illustrate her face in motion—animation while smiling. Her right eye is larger and higher than her left eye, and her right cheek is fuller and more round than her left cheek. According to the FLT, the asymmetry of her eyes is a "random" occurrence being due to DNA or embryology; whereas, her cheek asymmetries are a predictable occurrence based upon FLT and here show that her fetal lie position was LOA. In the animated views, it may be more easily observable that her right cheek 505 is heavier and less contoured than the left cheek and her nasolabial fold on the left cheek 506 is superiorly (upwards) heavier and deeper. In addition, due to the facial asymmetries, as shown in photo 502, an observer's eye is drawn down by the right side of the face, and drawn up (towards the facial midline) on the left side of the face.

In particular the facial asymmetries illustrated below in Table 1 are categorized according to hypothesized FLT LOA predictable outcomes versus random occurrences based upon DNA/Embryology or yet unknown. For ROA fetuses, the predictable outcomes are the same—just reversed as to side (hemi-face).

TABLE 1

| Facial Feature | Description of asymmetry | FLT predictable | DNA/embryology |
|---|---|---|---|
| Eyes | One eye opening is larger, one eye is higher, and one eye is deeper set than the other | | DNA/embryology - random occurrence |
| Eyes | One eyebrow is higher or more arched | | DNA/embryology - random occurrence |
| Cheek | The R cheek is fuller, less contoured with rounder jowls. | FLT predictable occurrence | |
| Cheek | R cheek has a boxier or wider jawline from the mental protuberance to the gonial angle | FLT predictable occurrence | |
| Cheek | The L cheek is more contoured or skeletonized, with less jowling and | FLT predictable occurrence | |

TABLE 1-continued

| Facial Feature | Description of asymmetry | FLT predictable | DNA/embryology |
|---|---|---|---|
| | subcutaneous fat (SQ), has a straighter angled jawline from the mental protuberance to the gonial angle | | |
| Cheek | One cheekbone is higher | | DNA/embryology - random occurrence |
| Mouth | Mouth at rest - The L side is thinner, more linear, and less full, and most often pulls to the L side superiorly and more laterally than the R side. The R upper lip hangs lower than the L and involutes onto itself (e.g., showing less pink lip) from pressure from the heavier R cheek | FLT predictable occurrence | |
| Mouth | Mouth smiling: The L hemi-smile pulls laterally and superiorly, making it more smirky, or crooked. The full smile pulls the L upper and lower lip thinner and more linear than its plumper and squarer R upper lip (which involutes onto itself and hangs lower). | FLT predictable occurrence | |
| Naso-labial Fold | The L nasolabial fold is superiorly heavier and deeper, especially on animation | FLT predictable occurrence | |
| Hemi-face | The R hemi-face as a whole is larger | FLT predictable occurrence | |

Of note, as more research is done and experience provided, some of the facial asymmetries currently categorized as random occurrences may prove to be predictable.

Fetal Lie Theory may also provide a hypothesis as to causes of certain birth defects—such as cleft lip and palate. Although currently the cause of cleft lip and palette are unknown, in most cases this defect occurs greater on the left versus the right side of a baby's face. LOA can be used to explain such occurrences assuming that the fetus' head was even more rotated laterally again the maternal pelvis. The anterior pressure point would be on the mouth, vs the jawline, and it would it prohibit the neural tube from properly closing at that pressure point.

Although some birth defects may be treatable in the same way as FLT predicted facial asymmetries, because they are highly patient dependent, as described with reference to FIG. 1, the Symmetry Solutions Method of Treatment excludes such defects.

Figure 6:
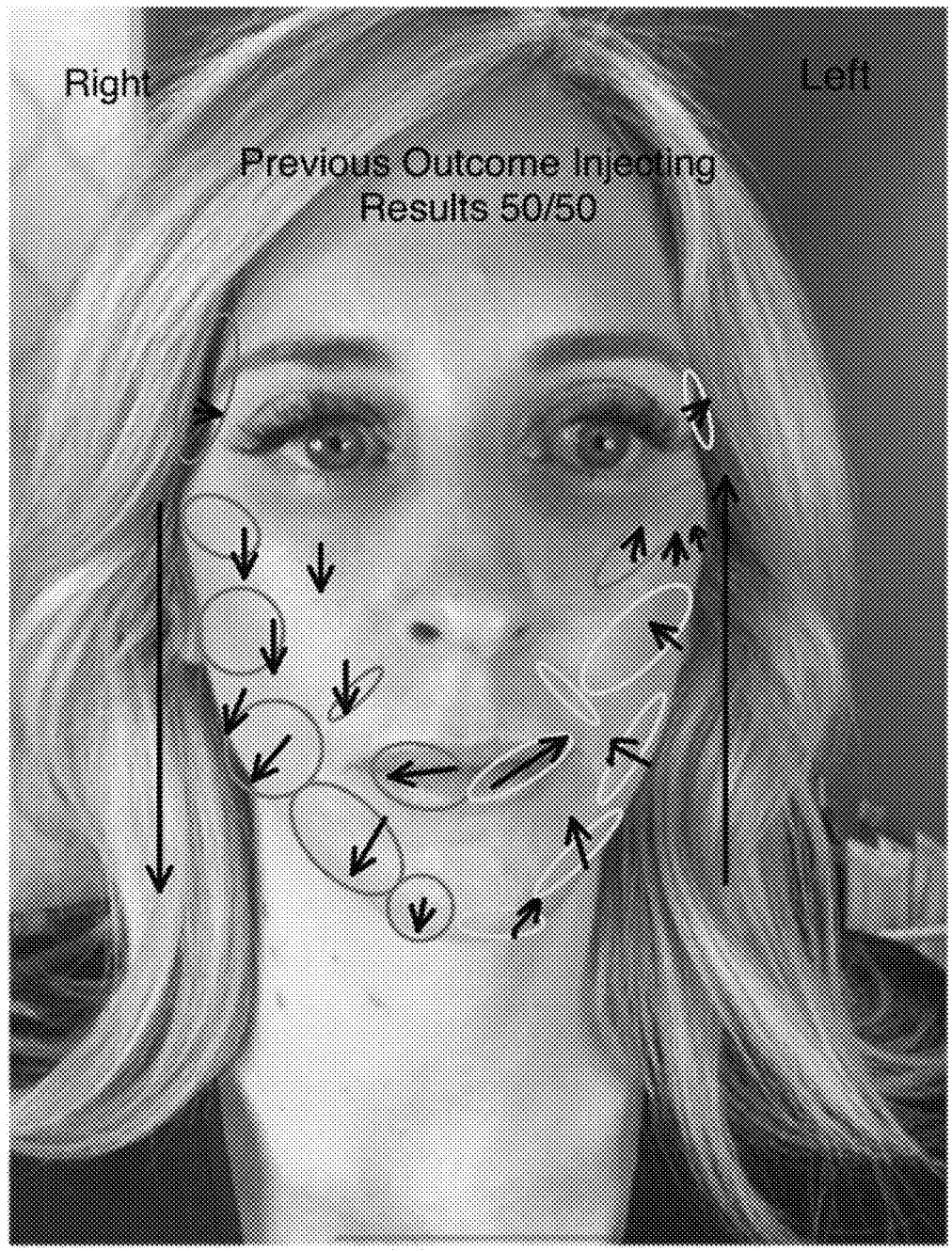
FIG. 6 illustrates an example of a patient with LOA predictable asymmetries whose facial sides has been injected equally.

In summary, the Fetal Lie Theory can be used to predict certain facial asymmetries such as that in the majority of patients being treated with dermal filler injections (due to the most common LOA position), the left side of the face is smaller, more contoured than the R, and is pushed laterally (back towards the ear) and superiorly (upwards). Logic dictates that injectors should either 1) use more dermal filler product on the left zygoma (cheek area) then the right—to match the heavier right side (since we are adding filler); or 2) inject both sides equally as taught in the current state of the art. However, we have found that both corrections are wrong—as they will cause an observer's eyes to be pulled in the wrong directions and result in further apparent asymmetry. FIG. 6 illustrates an example of a patient with LOA predictable asymmetries whose facial sides has been injected equally. The circles indicate areas of injections, and the black arrows illustrate where an observer's eyes are drawn. By filling both facial sides equally, the asymmetries are exacerbated and the face looks further out of alignment.

As described in the overview of FIG. 1, the Symmetry Solutions Method of Treatment corrects FLT predicted asymmetries based upon a level of severity determined by an asymmetry severity scale guide ("ASSG") developed as a result of understanding the role of FLT in influencing facial asymmetries. Once the severity level is determined (as either a Grade 1 or Grade 2 asymmetry), the SSM can be used to prescribe dermal filler injection treatment. (See steps 106-109 of FIG. 1.) In addition, the guidelines encompassed by SSM can be used as a guide to correct a failed or incomplete prior injection treatment.

FIG. 7 illustrates the Symmetry Solutions Method of Treatment Asymmetry Severity Scale Guide which provides guidelines for grading and methods of correction. In FIG. 7, the Asymmetry Severity Scale Guide (ASSG) 700 contains three (3) different severity grades (grades 701) to be determined by an injector; namely "mild" (row 705), "moderate" (row 706), and "severe" (row 707). For each grade, ASSG 700 shows a description 702 of the grade, including a percentage of population where applicable; the corresponding FLT position 703 deemed to be responsible for the grade, and the overall formula 704 for applying dermal filler to reduce asymmetries. The goal of injectors is typically to restore a face to a more youthful look of that patient—namely the own patient's baseline. Thus, the reducing of asymmetries due to the Fetal Lie Theory and exaggerated by age, sun damage, and external factors from the breakdown in fat, connective tissue and laxity of ligaments and skin contributes to restoring the patients overall appearance to be more youthful.

The Mild asymmetry level, known as SSM Grade 1 or SS-G1 asymmetry, is found in approximately 4-5% of the population. These faces tend to have a good balance between facial angles and contours versus subcutaneous fat (Type A); tend to be very thin and narrow, with flat and minimal contour and less facial fat (Type B); or tend to be very round as their facial skull has undistinguished/undefined contour, with very heavy facial tissue (Type C). For example, Type A individuals typically have more facial angles/contours than SQ fat while still having a balance between the two, and the facial zones are in different planes with defined boarders. Type B individuals have face shapes that were changed after birth into a more symmetrical, flat and narrow image typically from external pressure from manually rotating the face side to side while with bones were still malleable. Type C individuals may be a very young person, or someone with undistinguished or undefined contour to their facial skull (i.e., flat bones), or one with very heavy facial tissue. It is difficult to see their bone structure as the transition zones are blurred.

Some individuals with mild asymmetry (Types A and B) are people who likely gestated breech, were born premature (<38 weeks) or by cesarean section due to other reasons than failure to descend into the birth canal. Types A-C and examples are discussed further with respect to FIGS. 10-12. According to the SSM, the injector needs to use approximately 15% more filler collectively applied to the facial zones on the more contoured side of the face than to the facial zones on the heavier side of the face. In some cases, the range may be as wide as 10-20% collectively more filler depending upon the particular nuances of how the patient responds to injection treatment, the quality and condition of the skin, absorption rate, etc. Typically for mild asymmetries, 15% more filler is applied collectively (in total on the more contoured hemiface than on the heavier hemiface). In addition, as noted above, approximately 10% more filler will be applied to the light reflective area on the heavier side than to the light reflective area on the more contoured side. In some SSM embodiments, the ROA situation is termed a counter position and designated by a grade SS-CP-G1 to distinguish between the more contoured side being the right side.

The Moderate asymmetry level, known as SSM Grade 2 or SS-G2 asymmetry, is found in approximately 93% of the population. Most individuals with Moderate asymmetry are typically unaware they have facial asymmetry, and are typically surprised when it is identified, or if aware, they are certain their asymmetry is caused from a traumatic facial injury or birth, sleeping on their face or solar damage. Individuals with moderate asymmetry are people who likely gestated LOA or ROA. These types and examples are discussed further with respect to FIG. 13. According to the SSM, the injector needs to use approximately 25% more filler collectively applied to the facial zones on the more contoured side of the face than to the facial zones on the heavier side of the face. In some cases, the range may be as wide as 21-30% collectively more filler depending upon the particular nuances of how the patient responds to injection treatment, the quality and condition of the skin, absorption rate, etc. Typically for moderate asymmetries, 25% more filler is applied collectively (in total on the more contoured hemiface than on the heavier hemiface). In addition, as noted above, approximately 10% more filler will be applied to the light reflective area on the heavier side than to the light reflective area on the more contoured side. In some SSM embodiments, the ROA situation is termed a counter position and designated by a grade SS-CP-G2.

The Severe asymmetry level, known as SSM Grade 3 or SS-G3 is found in approximately 2-3% of the population. Typically the person is aware of their facial asymmetry as it is most likely due to a troublesome pregnancy and may additionally have a genetic, pregnancy, or acquired syndrome unrelated to FLT that causes the observed asymmetries. Correction is made on a case-by-case basis and there is no predictable consistent asymmetries that can be treated by SSM. Injection is performed on a customized basis.

The particulars of the ASSG based injection plan are determined and identified for each patient during consultation through assessment, photographs, measurements, and inquiry, although most patients fall under SS-G2 (or SS-CP-G2) and are treated accordingly. Thus, with inconclusive or inconsistent evaluation results, the patient can be treated under an SSM G2 method of treatment (21-30% collectively more dermal filler applied on the more contoured hemiface and approximately 10% more dermal fille to the heavier side light reflective area than the more contoured side light reflective area).

Figure 8:
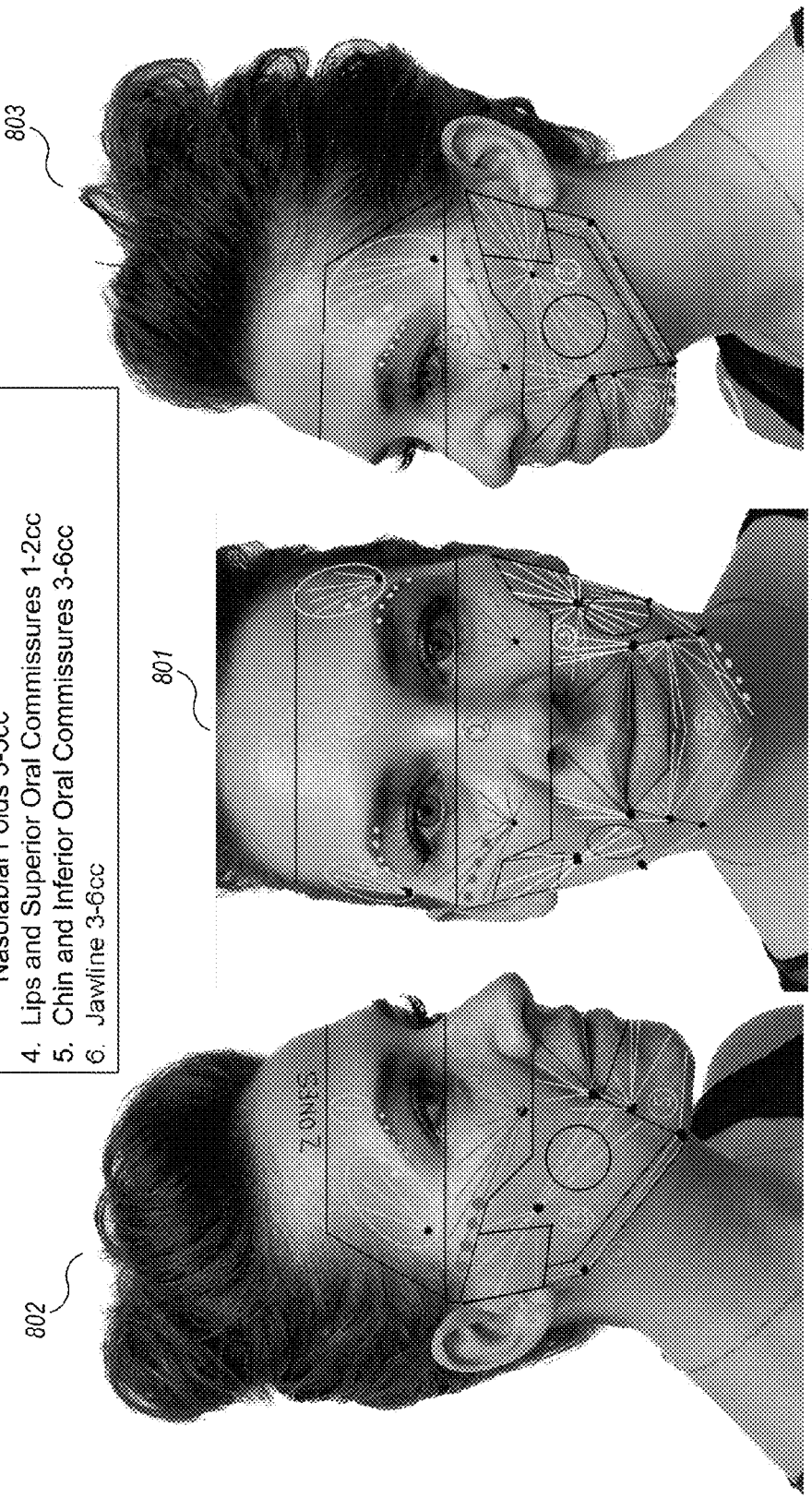
FIGS. 8 and 9 illustrate the SSM facial correction zones.
Figure 9:
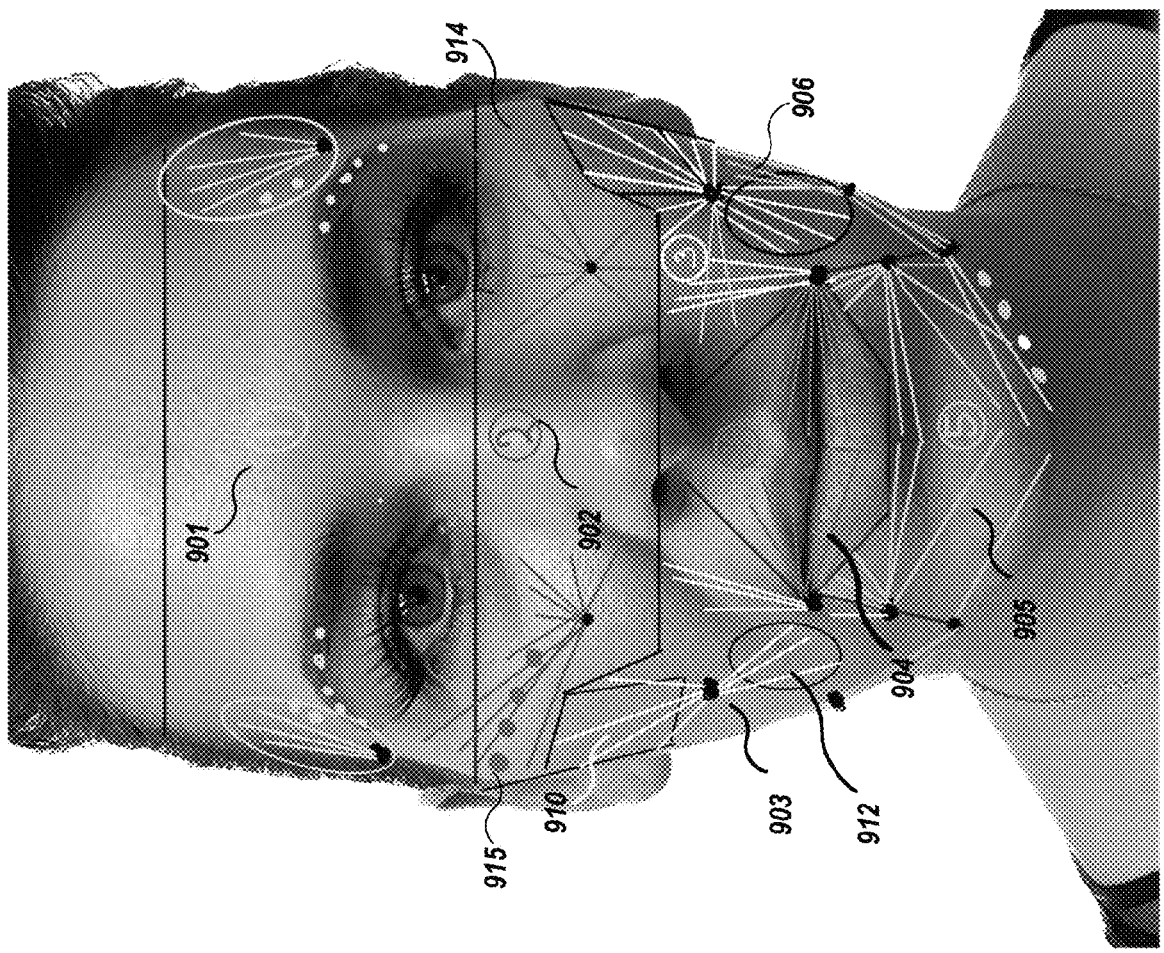

According to SSM, dermal filler injections are applied to one or more facial zones and in different sequences. FIGS. 8 and 9 illustrate the SSM facial correction zones. FIG. 8 shows the zones from a right side viewpoint 802, from a center viewpoint 801, and from a left side viewpoint 803. The zones are shown by black line borders and in color. A closeup diagram of the zones is shown in FIG. 9. Zone 1 901 (yellow) consists of the temple and brows; Zone 2 902 (blue) consists of the medial (i.e., towards face center) and superior and lateral (i.e., up and back towards ear) cheeks which include the light reflective area (blue dots); Zone 3 903 (white) consists of the inferior lateral cheek, preauricular fossa (the SSM cheek rectangle and cheek circle) and the nasolabial folds; Zone 4 904 (red) consists of the lips and superior oral commissures; Zone 5 905 (light blue) consists of the chin and inferior oral commissures; and Zone 6 906 (green) consists of the jawline. The zone color dots indicate serial injections of dermal filler with an injection needle; the black circles indicate a hole in skin where a canula is inserted and the colored rays emanating from the canula holes indicate the direction the filler is injected and the intended approximation of travel. The combination of injecting into both the cheek rectangle 910 and cheek circle 912 of Zone 3 present a set of locations unique to SSM.

Under SSM, the sequence of injection of dermal fillers makes a difference as well as the overall SSM technique of treating the more contoured side with more filler (overall) than the treatments to the heavier side of a patient's face. As well, injecting more dermal filler onto the Zone 2 light reflective area 915 to create more contour on the heavier side than the more contoured side is also unique to SSM. As described earlier, this is counterintuitive to both accepted logic (putting more filler in the more contoured zygoma to equal the heaver side zygoma) and traditional methods of injecting both sides of the face equally. As can be observed from FIG. 9, the serial injections 914 applied to the more contoured hemiface light reflective area of the zygoma are represented as smaller blue dots (indicating less dermal filler) than the serial injections 915 applied to the heavier hemiface which are represented as larger blue dots. The SSM protocol thus indicates that more dermal filler is (counterintuitively) applied to the heavier side light reflective area ("LRA") of Zone 2 than on the more contoured side light reflective area—even though, overall, more dermal filler is applied to the facial zones of the more contoured side (which is also counterintuitive). Of note, the medial zygoma 902 is treated separately from the LRA of Zone 2. Also, as described in FIG. 9, the sequence of injections to the various zones is important: Zones 1, 2, and 4 can be injected standalone or in any order. And, when part of the treatment, Zone 3 is injected after Zone 2; Zone 5 is to be injected after Zones 2, 3, and 4; and Zone 6 is to be injected after Zones 2, 3, 4, and 5. Results from example testing of SSM indicates that injections performed in such sequence result in more desirable outcomes for the patient. In particular, injecting the zygomas of Zone 2 before the cheek rectangle and circle of Zone 3 results in more contour control by lifting the cheek superiorly and laterally before equalizing the remainder of the cheek. The specific SSM guidelines for Zone 4 (lips and mouth) are described further below with respect to FIG. 22.

In general, the Symmetry Solutions Method of Treatment plan is based upon carefully balancing a number of factors including cost of dermal filler injections and the desire to return a patient's facial features to a more youthful appearance. Typically, the goal is to return a patient's facial features to their own individual baseline—often established using photos of a younger version of the patient and then injecting just a little more to create more contour since an observer's eye goes there first. During the SSM injection session(s), the injector makes adjustments to different zones based upon factors such as how the live tissue is responding (some tissue absorbs filler, plumps up or makes a change faster than others, etc.); how the lifting, projecting, contouring, and blending is actually resulting, not wanting to overfill; individual patient desires (injecting towards a baseline and not necessarily towards a fully corrected vision). Even with these individual zone adjustments, the overarching principle of SSM is to inject the more contoured side more than the heavier side and within the ranges of 10-20% for an ASSG grade 1 (SS-G1) face and 21-30% for an ASSG grade 2 (SS-G2). It is a further principle of SSM to inject more on the reflective light area (LRA) of the heavier side vs that of the more contoured side.

Injection Plan Example 1

As illustrated in FIGS. 8 and 9, dermal filler injections are applied to a patient with SS-G2 severity with the following amounts:
- 16 cc's overall with 9 cc applied to the more contoured side (L side) and 7 cc applied to the heavier side (R side); collectively approximately 29% (which is in the range of 21-30%) more filler volume on the more contoured side than the heavier side
- As noted by the size of the blue dots in the light reflective areas of Zone 2 914 and 915, LRA 915 has more dermal filler injected applied to LRA 914.

General Guidelines for Injection Plans for SS-G1 and SS-G2:

The following general guidelines are provided for producing an SSM injection plan for patients with SS-G2 severity. Of note, these guidelines are for correcting asymmetry where no prior corrections (from previous dermal filler injections) have been made (e.g., an injector is not trying to correct prior work).

Ranges of dermal filler for injections include:
Zone 1 2-3 cc
Zone 2 2-4 cc, with more cc applied to the heavier posterior, superior, lateral zygoma (LRA) than the more contoured side corresponding area
Zone 3 3-5 cc
Zone 4 1-2 cc
Zone 5 3-6 cc
Zone 6 3-6 cc Asymmetry Severity Guide Examples There are three different types of SSM Grade 1, or "Mild" asymmetry according to the Symmetry Solutions Method of Treatment. FIG. 10 illustrates annotated photos of a Type A SSM Grade 1 (SS-G1) mild level of asymmetry. Type A shows more contour than subcutaneous (SQ) fat while still having a balance between the two, and the facial zones are in different planes with defined borders. As explained earlier, SS-G1 or mild asymmetry is present in approximately 4-5% of the population and thus these individuals are outliers. This asymmetry is not easily recognized by the average observer. Elizabeth Hurley 1001 was once considered by a computer analysis to be the most symmetrical and beautiful woman in the world. You can see the contour of her bones. She has more contour than "juicy"—meaning that her face has more facial angles than fat or lack of angles, and that her facial zones are in different planes. Her facial asymmetry still abides by the Fetal Lie Theory. Annotated photograph 1002 illustrates the injection zones on her face. Annotated photograph 1003 shows the SSM injection plan of applying dermal filler to Zones 1-6 whereby, to reduce asymmetry, collectively (in sum) more filler volume, in a range of 10-20%, with typically approximately 15%, is injected on the left side of her face with approximately 10% more filler volume on the LRA of the right (heavier) zygoma than on the LRA of the left (more contoured) zygoma. Total filler volume is approximately L side 5 cc and R side 4 cc. Note that exact measurements are not needed to assign a patient to the Asymmetry Severity Scale Guide. The measurements shown in FIG. 10 demonstrate to the observer that asymmetry in the hemifaces is present in the photo but these are not generally taken into consideration for determining the ASSG level of severity. In some embodiments of the SSM, such measurements may be used to help devise an actual injection plan and assign initial volumes to be injected in the various zones.

FIG. 11 illustrates annotated photos of a Type B SSM Grade 1 (SS-G1) mild level of asymmetry. Type B individuals have a narrow, flat face with less contour and less facial SQ fat. Facial zone contours blur between zones. Individuals such as shown in annotated photo 1101 were probably born prematurely. The person's face shape likely was changed after birth (e.g., in the NICU) into a more symmetrical, flat and narrow image from external pressure, which was caused by manually rotating the face side to side while the facial structural bones were still malleable. Annotated photograph 1102 shows the SSM injection plan of applying dermal filler to Zones 1-6 whereby, to reduce asymmetry, collectively (in sum) more filler volume, in a range of 10-20%, with typically approximately 15% is injected on the left side of her face with approximately 10% more filler volume on the superior LRA of the right (heavier) zygoma than on the LRA of the superior left (more contoured) zygoma. Total filler volume is approximately L side 5.4 cc and R side 4.7 cc.

Figure 12:
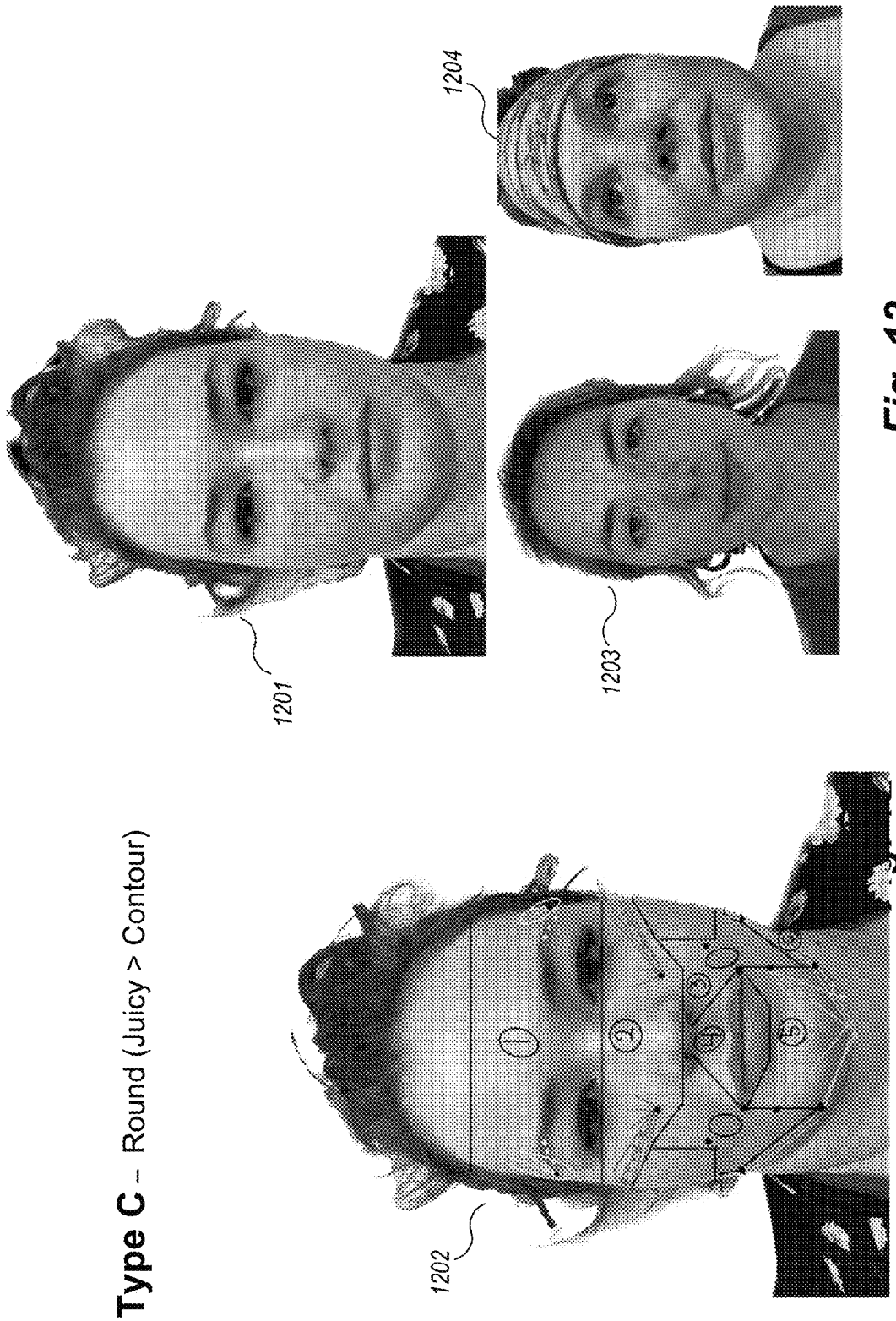
FIG. 12 illustrates annotated photos of a Type C SSM Grade 1 (SS-G1) mild level of asymmetry.

FIG. 12 illustrates annotated photos of a Type C SSM Grade 1 (SS-G1) mild level of asymmetry. Type C individuals have a very round face lacking contour (or "flat" bones). Once cannot see the contour of the cheek bones, and there is no transition of the planes moving from one zone to another. Individuals such as shown in annotated photo 1201 could be a very young person or one with very heavy facial tissue with what is often termed a "baby-face" (or their facial skull has undistinguished/undefined contour). The facial asymmetry of these individuals follow the Fetal Lie Theory, but you cannot see their bone structure as the transition zones are blurred from one to the next. Annotated photograph 1102 shows the SSM injection plan of applying dermal filler to Zones 1-6 whereby, to reduce asymmetry, collectively (in sum) more filler volume, in a range of 10-20%, with typically approximately 15% is injected on the left side of her face with approximately 10% more filler volume on the superior LRA of the right (heavier) zygoma than on the LRA of the superior left (more contoured) zygoma. Total filler volume is approximately L side 5.75 cc and R side 5 cc.

Figure 13:
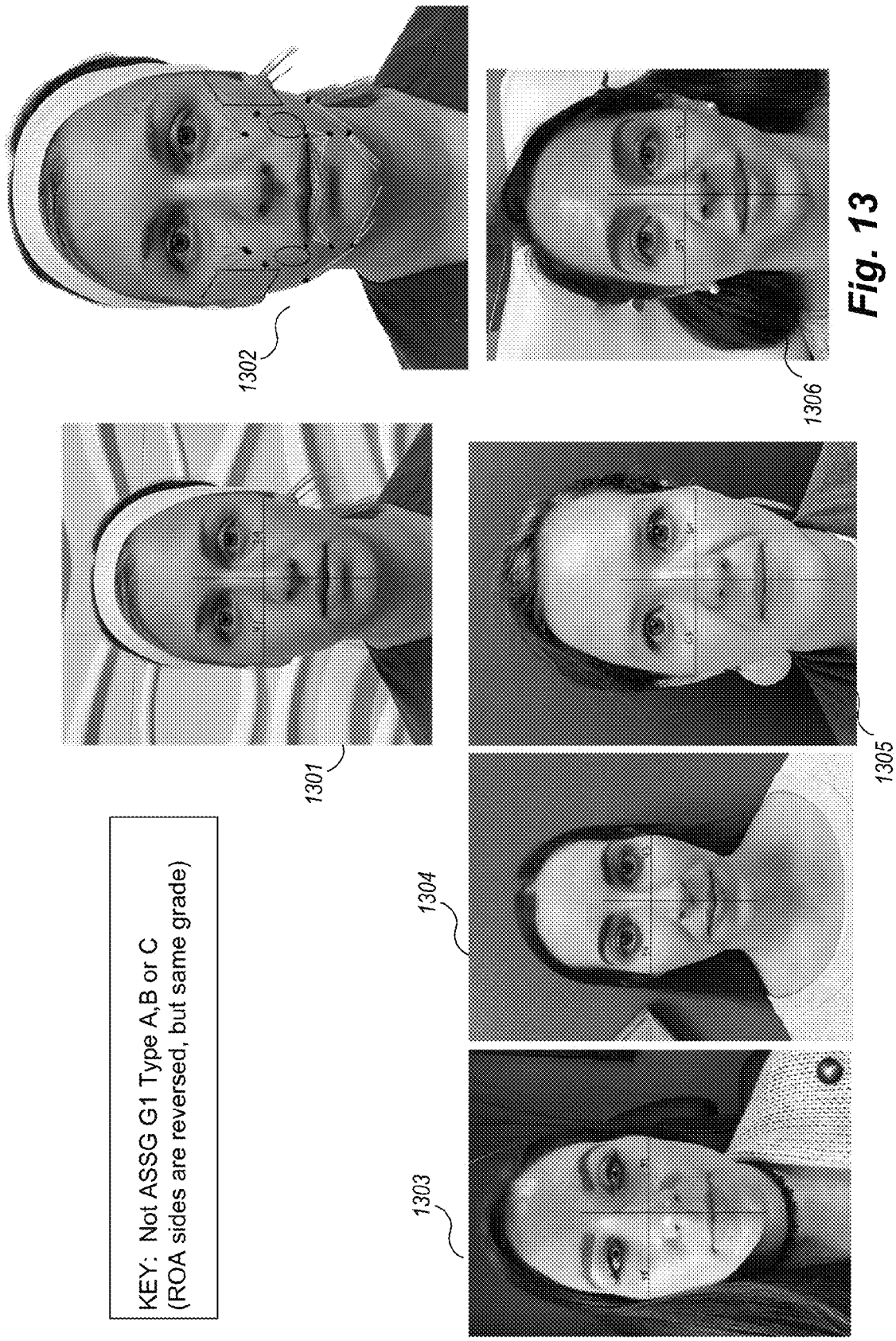
FIG. 13 illustrates annotated photos of a SSM Grade 2 (SS-G2) moderate level of asymmetry.

FIG. 13 illustrates annotated photos of a SSM Grade 2 (SS-G2) mild level of asymmetry. Individuals such as shown in annotated photos 1301-1306 represent approximately 93% of the general population. Most people in this category such as the individual in annotated photo 1301 are unaware they have facial asymmetry, and are typically surprised when it is identified, or, if aware, they are certain their asymmetry is caused from a traumatic birth, facial injury, sleeping on their face or solar damage. As a default or when in doubt, an injector should use this SSM associated with SS-G2 level of severity as it is the most prevalent in the world. The facial asymmetry of these individuals shown in photos 1301-1306 is consistent with those who gestated in the LOA position according to Fetal Lie Theory. (Those who gestated in the ROA position have more contour on the right hemiface and a heavier left hemiface and treatments are reversed.) Birth could be vaginal or cesarean. They are identified as not being in ASSG G1 Type A, B or C. As a whole these individuals need more contour on their heavier (R) side of the face and more blending of fat with the zygoma contour on the more contoured (L) side of their face. In many instances, they need more contour on the light reflective area in Zone 2 on their heavier (R) side of the face and more blending of the overly contoured Zone 2 of the more contoured (L) side of their face by adding filler to Zone 3 of the more contoured side. Annotated photo 1302 shows the SSM injection plan of applying dermal filler to Zones 1-6 whereby, to reduce asymmetry, collectively (in sum) more filler volume, in a range of 21-30%, with typically approximately 25% is injected on the left side of her face with approximately 10% more filler volume on the superior LRA of the right (heavier) zygoma than on the LRA of the superior left (more contoured) zygoma. Total filler volume is approximately L side 5 cc and R side 4 cc.

As explained above an individual who is identified as birthing ROA instead of LOA is termed a "counter position" in that the more contoured face is the right hemiface and the heavier side is the left face. All of the foregoing example injection plans for G1 (mild) and G2 (moderate) and G3 (severe) can be applied with "L" side values becoming "R" side values, and "R" side values becoming "L" side values. FIG. 14 illustrates annotated photos of a SSM Grade 2 (SS-G2) mild level of asymmetry for an individual having a counter position fetal lie. That is, annotated photos 1401-1404 illustrate an individual whose right side of her face is more contoured while the left side of face is heavier. Approximately 3% were on the ROA position during late gestation with the maternal pelvis resting on the right (R) fetal face. These individuals are treated according to the SSM as described with reference to FIGS. 10-13 but with the larger dermal filler volume and mirrored technique on the right hemiface (the more contoured side). Annotated photo 1404 shows the SSM injection plan of applying dermal filler to Zones 1-6 whereby, to reduce asymmetry, collectively (in sum) more filler volume, in a range of 21-30%, with typically approximately 25% is injected on the right more contoured side of her face with approximately 10% more filler volume on the superior LRA of the left (heavier) zygoma than on the LRA of the superior right (more contoured) zygoma. Total filler volume is approximately R side 7.5 cc and L side 6 cc.

Comparison of Results Injecting Filler Equally Vs Correcting Using SSM Guidelines:

As described, current state of the injection art teaches to treat both sides of an individual's face equally. There are consequential poor outcomes as a result of injecting filler equally on both sides, namely (the parenthetical hemiface examples assume LOA Fetal Lie and not a counter position—if ROA, the examples are the opposite):

The heavier (e.g. R) hemiface will remain heavy, drawing our eye down to the heavier (e.g., R) Z3 jowl due to lack of contour on the heavier side (R) Z2 zygoma, and the heavier (R) Z3 zygoma/preauricular fossa (cheek square and circles) transition will be too full and without contour.

The more contoured (L) Z2 hemiface will be too contoured, drawing our eye up to the more contoured side (L) skeletonized and sharp zygoma. The more contoured (L) Z3 preauricular space will be hollow, and the zygoma/preauricular fossa transition will be sharp.

The more contoured (L) lip will be too thin and linear, especially on animation.

The more contoured (L) Z3 nasolabial fold (NSF) will be deeper and more creased than the heavier side (R), especially on animation.

Compared to the heavier and boxier (R) side, the more contoured (L) side Z5 chin will be thinner, and the more contoured side (L) Z6 menton (the lowest point of the chin) to gonial angle (along the jowl) will be more linear and thinner than it's R heavier counterpart.

The injector will have created more asymmetry because our eye is first drawn to more contour (the more contoured (L) side), which our brain finds more interesting and pleasing than roundness, fullness and lack of contour (on the heavier (R) side).

The patient will point to the more contoured (L) hemiface and tell you they want the heavier (R) side to match.

Again, for an ROA Fetal lie position, these outcomes are mirrored right for left and left for right.

As mentioned earlier, prior injection techniques teach treating a patient's face equally on both sides and to ignore the asymmetry (referred to herein as the "50:50" technique). It is noteworthy that the SSM techniques of overall more filler on the more contoured side, more filler to the light reflective area on the heavier side, and blending on the cheek rectangle and circle may be incorporated when trying to complete or correct a patient that has already receive a 50:50 correction done. However, the overall percentage of correction percentages do not typically apply (approximately 15% and 25% to SS-G1 and SS-G2, respectively) because filler has already been added to the patient's face and oft times in unknown quantities. In addition, since the injector is not starting from a blank canvas not all zones may need addressed. Under SSM, more dermal filler is applied overall to the countered side—whether applied earlier or to correct prior work. Depending upon the prior work performed, the injector will probably need to apply more filler to the LRA of the heavier hemi face to create more contour as well as apply more filler to the contoured cheek rectangle and circle to create more blend. Accordingly, the following examples show injection plans based upon the SSM rules and guidelines but without reference to amounts.

Incomplete Outcome and Correction SS-G2: Example 2

Figure 15:
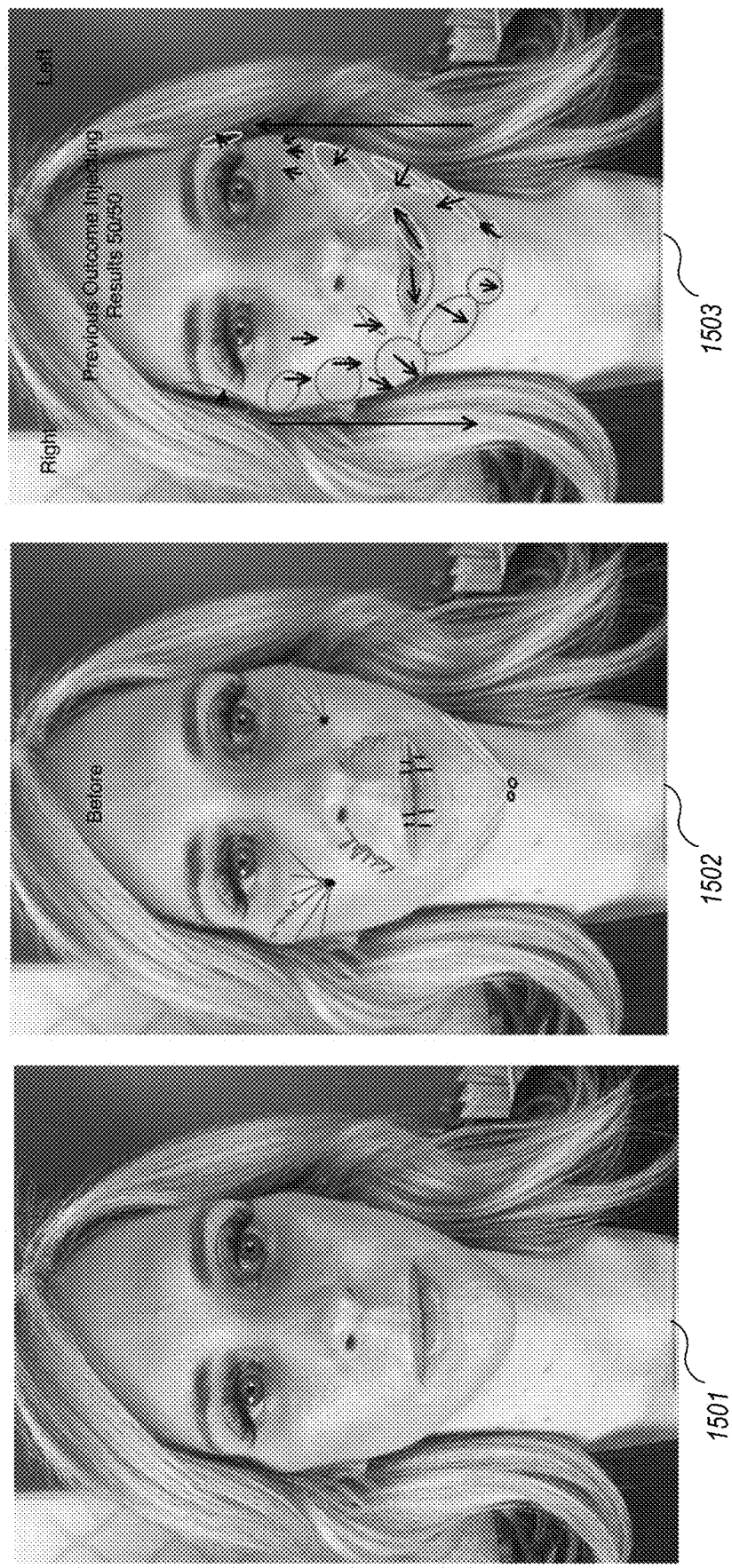
FIG. 15 illustrates an example of injection of dermal filler equally across both zygomas.

FIG. 15 illustrates an example of injection of dermal filler equally across both zygomas. Annotated photos 1501-1503 illustrate prior technique. An injection plan is shown in photo 1502 to inject both sides of her face equally. Photo 1503 shows the outcome achieved according to the plan shown in photo 1502, namely an observer's eye is drawn down on the heavier side of the face (see arrows on right hemiface) and drawn up on the contoured side of the face (see arrows on left hemiface). This results in exaggerated asymmetry.

Figure 16:
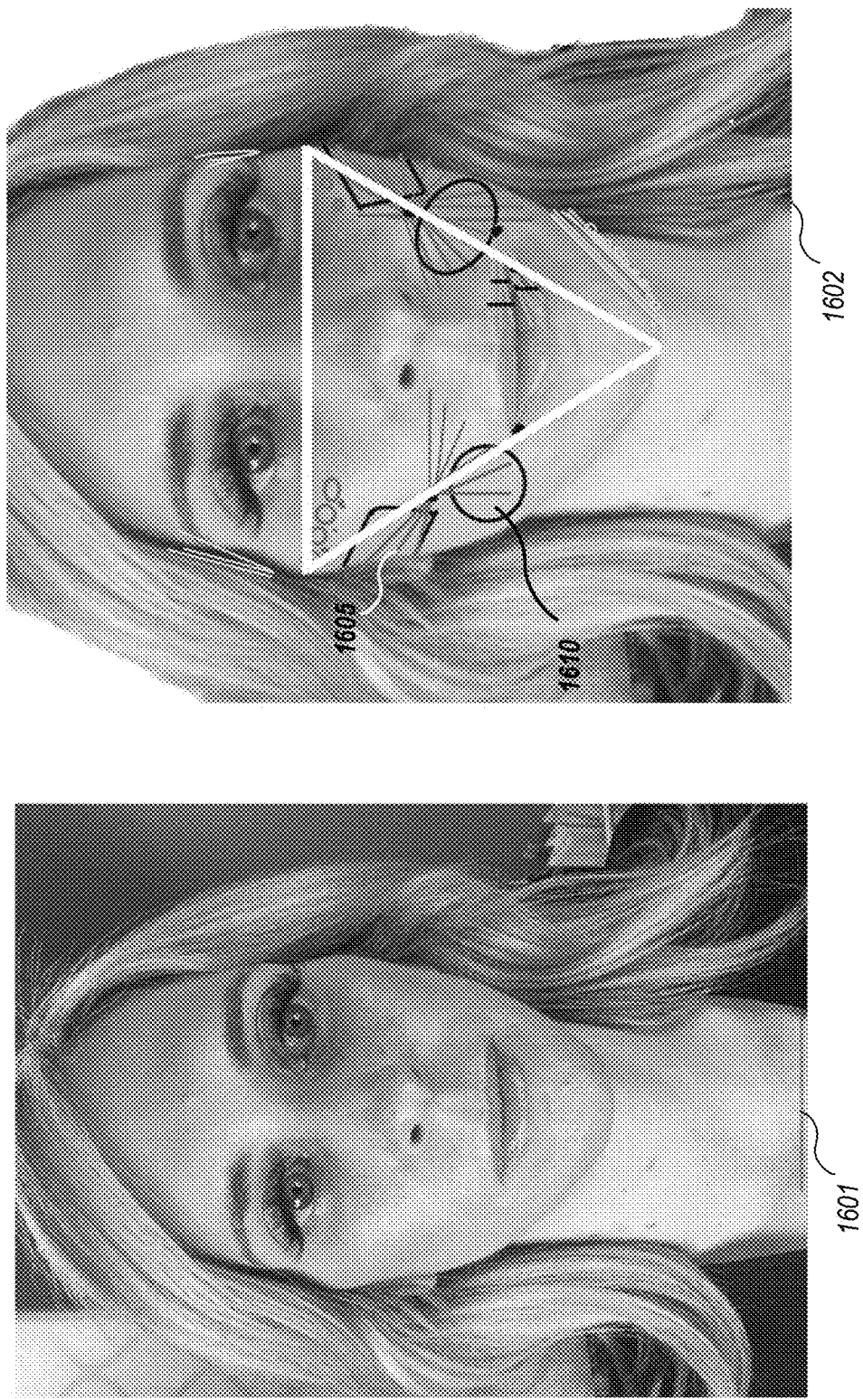
FIG. 16 illustrates a more optimal correction plan achieved through application of the Symmetry Solutions Method of Treatment techniques.

FIG. 16 illustrates a more optimal correction plan achieved through the application of the Symmetry Solutions Method of Treatment techniques. First, the patient 1601 is evaluated to determine a severity grade of SS-G2 (moderate asymmetry). Then an injection plan is formulated, as illustrated in photo 1602 to inject dermal filler to result in more filler on the more contoured side—here the left hemiface. The injection plan in 1602 shows that the heavier R side of the mid and lower face needs a superior (up) lifting, contouring procedure performed to zones Z2 and Z3 (refer to FIGS. 8 and 9). The more originally contoured L side of the mid and lower face needs a blending, softening, inferiorly, equalizing procedure. More product needs to be placed in the L Cheek Rectangle 1605 and Cheek Circle 1610 in zone Z3. More product needs to be placed in the L lip zone Z4, chin zone Z5, and jowl angle zone Z6. To achieve predictable and consistent outcomes, each side of the face is to be treated differently, with the proposed plan. This is in direct contrast to prior methods of treatment. The white triangle overlay annotated photo 1602 represents the "Triangle of Youth" and illustrates an optimum area for directing an observer's eye superiorly to the maximum, lateral projection of the cheeks away from the heavier jowls. This creates a more youthful appearance.

Note that the cheek rectangle area 1605 is defined by a rectangle having a width from the top of the earlobe medially extending parallel to the zygoma approximately 1.5-2 inches and having a height extending from the top down to the bottom of the earlobe. The cheek circle 1610 area is medial to the masseter, inferior to the cheek zygoma and superior to the jaw. It is the area or donut that when you press on the cheek there is nothing against it (e.g., no cheek or jawbone). That area is lax and the circle's diameter is approximately 1.5-2 inches. The SSM specifies injecting filler into this area improves skin texture and reduces jowling to blend, pull laterally, soften, and equalize the tissue in Zone 3.

Incomplete Outcome and Correction SS-G2: Example 3

Figure 17:
FIG. 17 illustrates another example of injection of dermal filler equally across both zygomas.

FIG. 17 illustrates another example of injection of dermal filler equally across both zygomas. Annotated photos 1701-1703 illustrate prior technique. Photo 1701 shows the patient's face prior to any treatment. Patient complained of a hollow lower face and sharpened zygoma. Traditional (prior art) plan would involve 2 syringes of filler spread equally over both cheeks in zone Z2 to lift the jowls. Photo 1702 shows the results after 1 syringe was injected evenly over each zygoma in zone Z2. Patient looked worse. She felt her L cheek was very sharp and the filler made her look like a skeleton. Annotated photo 1703 validates the patient's observations. True, the eye is drawn up to the lateral zygoma Z2 (see line 1720) and away from the jowls in zone Z5, but it makes her asymmetry worse by hollowing out the L cheek square and circle in zone Z3 (see annotation 1710).

Figure 18:
FIG. 18 illustrates a more optimal correction plan achieved through application of the Symmetry Solutions Method of Treatment.

FIG. 18 illustrates a more optimal correction plan achieved through application of the Symmetry Solutions Method of Treatment. Annotated photo 1801 illustrates that by predicting the asymmetry, knowing that the L zygoma Z2 is more contoured, filling in the preauricular fossa zone Z3 (cheek rectangle and cheek circle) of the more contoured side will marry the void of the L preauricular fossa to the contour of the L zygoma creating more symmetry. This patient is so hollowed, that she could benefit from the cheek rectangle and circle bilaterally with L side >R side in volume.

Incomplete Outcome and Correction SS-G1, Type C: Example 4

Figure 19:
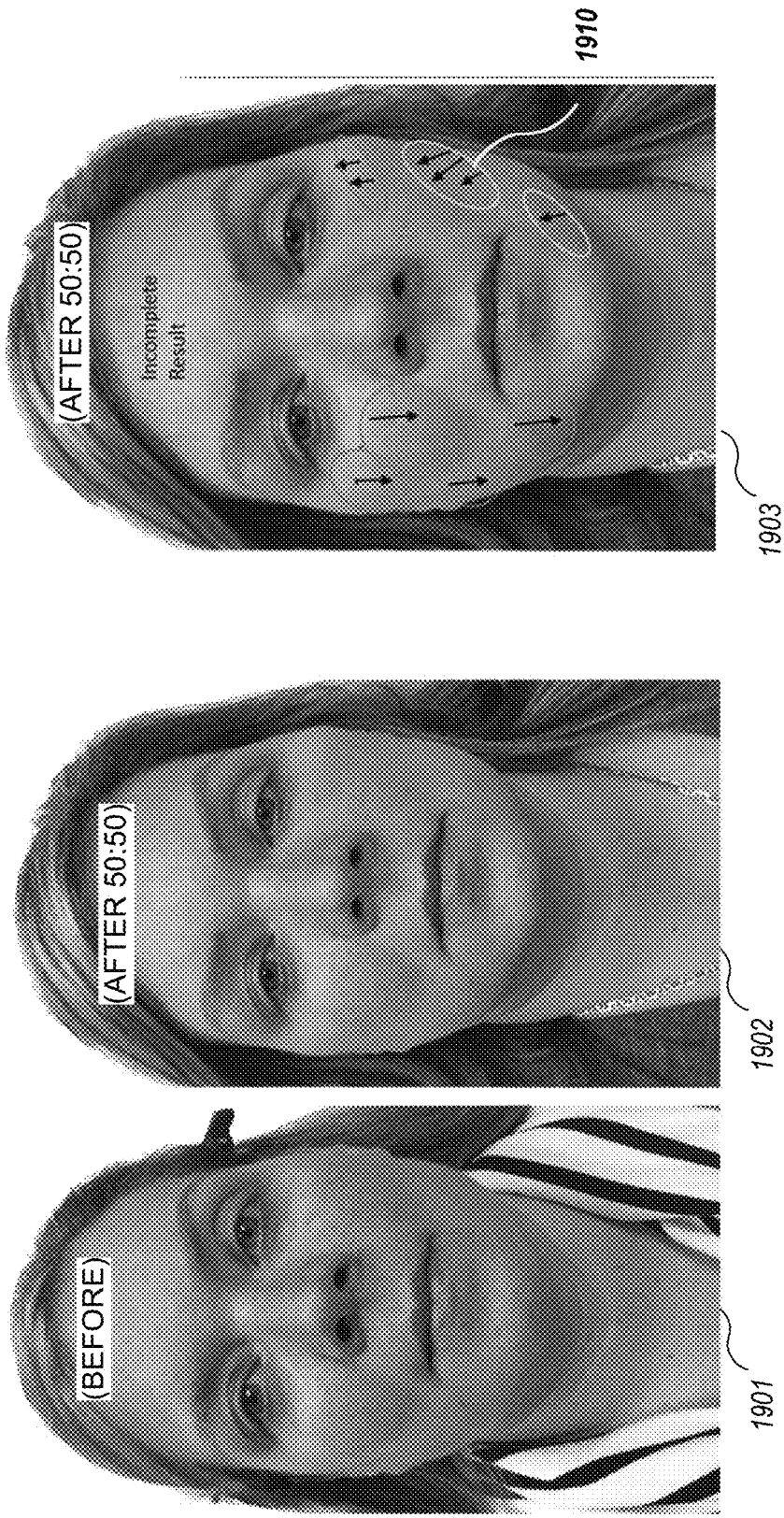
FIG. 19 illustrates another example of injection of dermal filler equally across both zygomas.

FIG. 19 illustrates another example of injection of dermal filler equally across both zygomas. Annotated photos 1901-1903 illustrate prior technique. Photo 1901 shows the patient's face prior to any treatment. The patient was injected equally across both cheeks with 3 syringes of filler. It is apparent from FIG. 1903 that the contour of the L zygoma hollows out the preauricular fossa (1910), creating more asymmetry, while the R cheek remains heavy and virtually unchanged.

Figure 20:
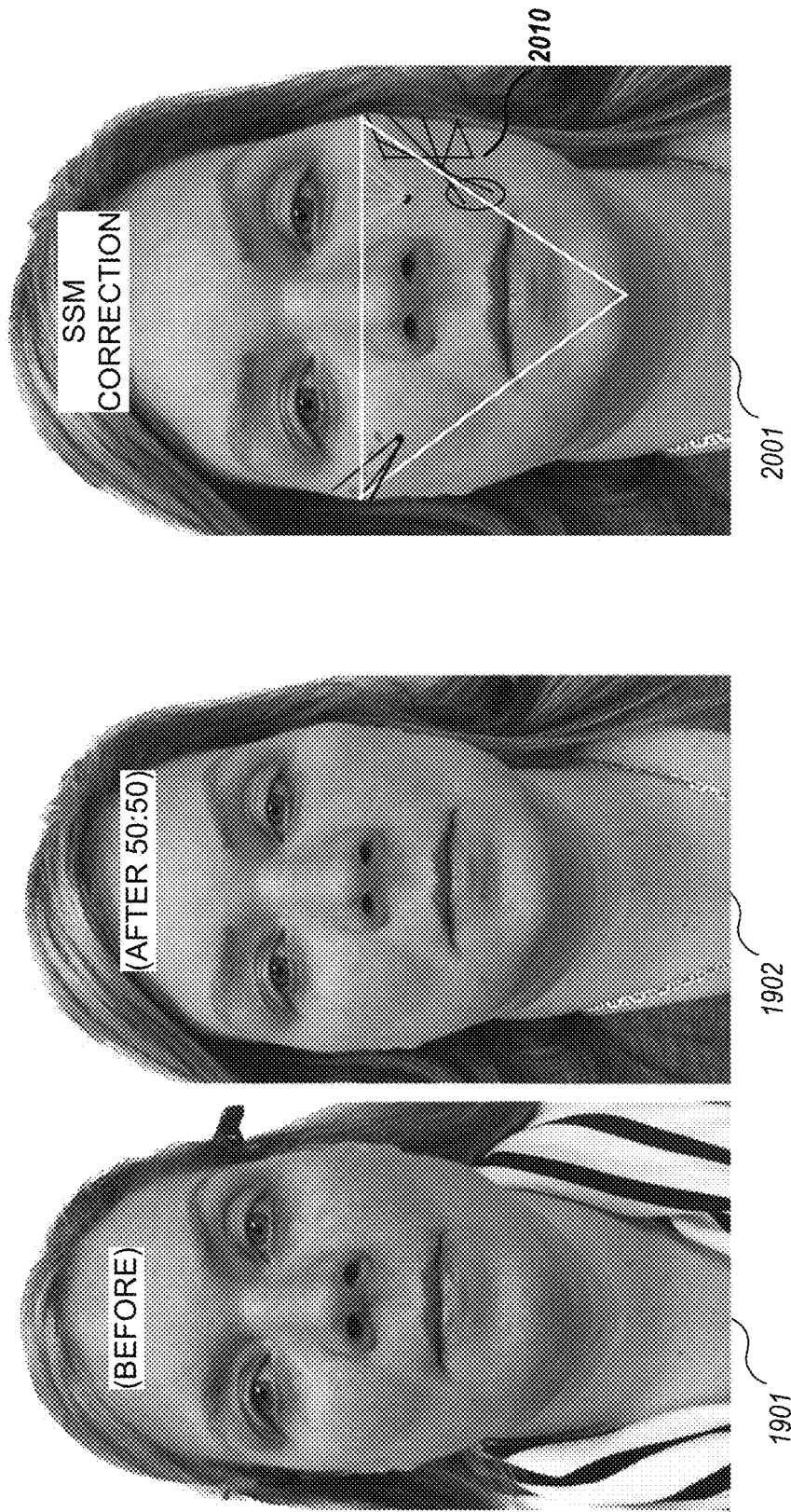
FIG. 20 illustrates a more optimal correction plan achieved through application of the Symmetry Solutions Method of Treatment.

FIG. 20 illustrates a more optimal correction plan achieved through application of the Symmetry Solutions Method of Treatment. Annotated photo 2001 illustrates that by predicting the asymmetry, adding more contour to the light reflective area of the heavier (R) side (the blue dots), will create a lift in the heavy R jowls drawing the viewer's eye up. Adding the cheek rectangle and circle with some medial cheek volume will equalize the overly contoured L zygoma.

Full Face Symmetry Solutions Method of Treatment for SS-G2 Example 4

Figure 21:
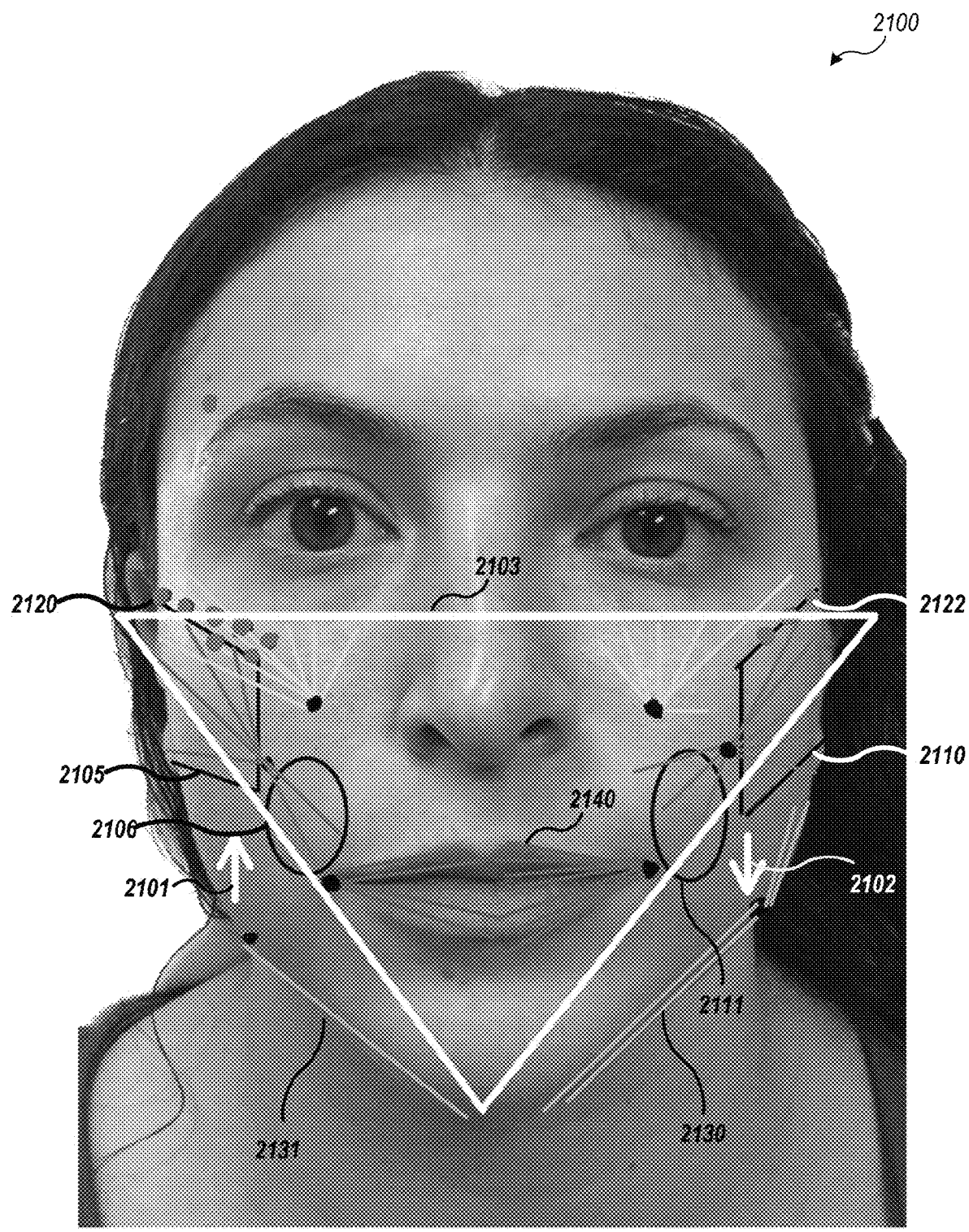
FIGS. 21-22 illustrate an example of using the Symmetry Solutions Method of Treatment to consistently correct asymmetry produced predictably from an LOA Fetal Lie position.
Figure 22:
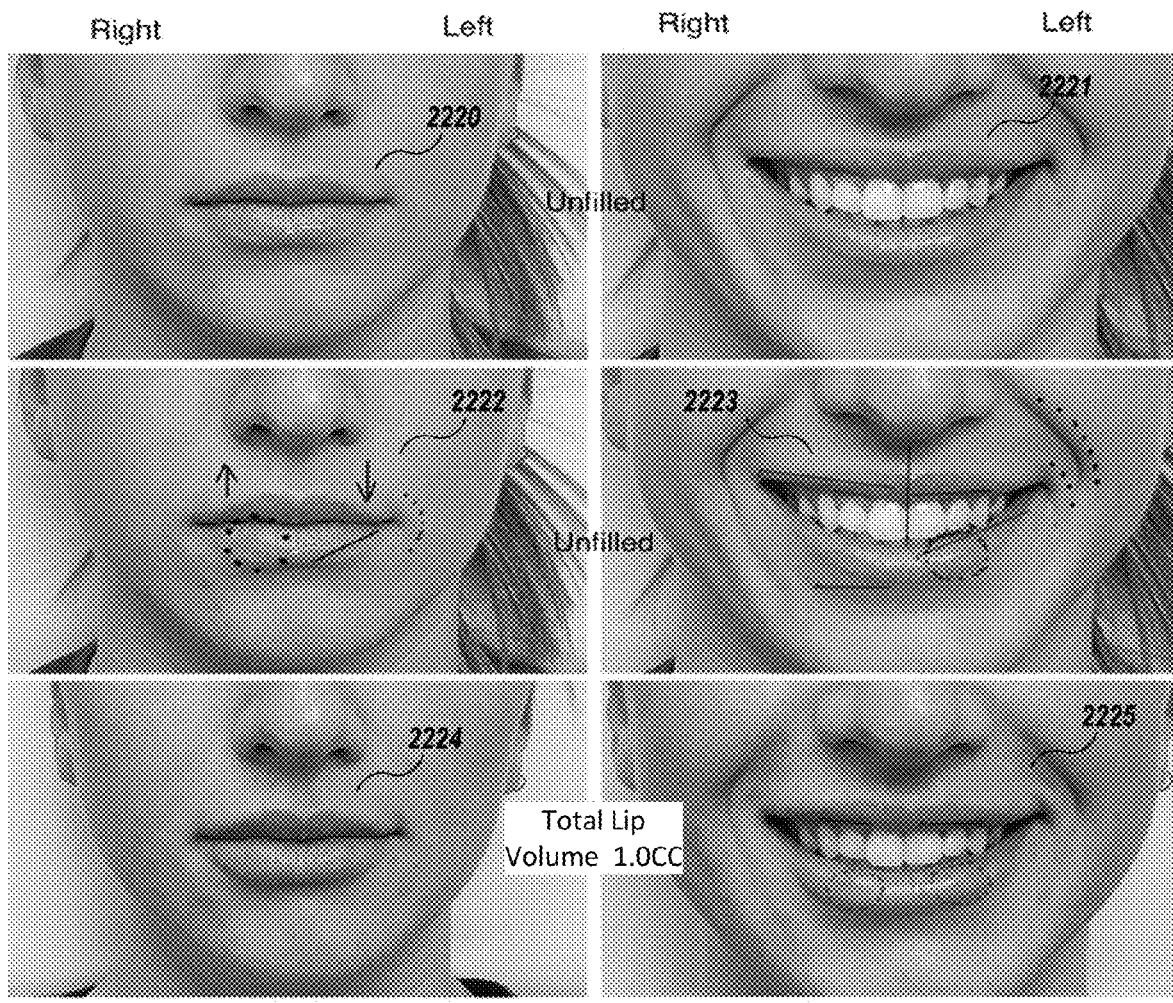

FIGS. 21-22 illustrate an example of using the Symmetry Solutions Method of Treatment to consistently correct asymmetry produced and predictable from an LOA Fetal Lie position. FIG. 21 exemplifies the overall injection plan for an SS-G2 full face corrective solution. In summary, then heavier R side of the mid and lower face needs a superior lifting, contouring procedure. The more contoured L side of the mid and lower face needs a blending, softening, inferiorly, equalizing procedure to reduce the appearance of asymmetries.

In particular, to accomplish these results, the SS-G2 patient collectively needs approximately 25% more filler volume on the more contoured side (L side here) with more filler on the superior light reflective area of the heavier side (R side here) than on the light reflective area of the more contoured (L) side. In this example, 3 cc of dermal filler are used on the R side, and 4 cc on the left side. More product is needed on the light reflective area of the heavier side R Z2 (2120, which can be observed from the greater and bigger number of blue dots), to lift up the fuller jowl R Z3 (including the cheek areas 2105-2106) to match the contour on the skeletonized left side light reflective area L Z2 (2122) and to pull inferiorly the heavier cheek creating more contour in Zone 3 on the heavier side.

This is where the injector desires to trick the brain and draw the eye to gaze superiorly at the inverted Triangle of Youth (2103) away from the jowls R Z3 (see directional arrow 2101). The inverted triangle (2103) represents the optimal direction we want the observer's eyes to be lead—from the tip of the triangle at the chin upwards. If instead more product is injected on the skeletonized light reflective area of L Z2 (2122), the LRA will become MORE skeletonized, not more voluminous, contrary to logic. The end result would be an extremely contoured L Z2 (2122), and a heavy, fat, off balanced R Z3—not desirable.

Next the injector injects dermal filler into the L Z3 (Cheek Rectangle 2110 and Circle 2111) blending the contoured zygoma and the cheek hollowing.

The injector may need to add volume to the L Z5-6 (chin and jaw) if the asymmetry is severe. This will draw the observer's eye inferiorly (downward in the 2102 direction) on the L hemiface and superiorly (upward in the 2101 direction) on the R side, balancing the two hemifaces.

Under SSM, the lips 2140 are typically injected and planned for specifically (see FIG. 22). More dermal filler is needed on the L Z4 side, and the injector needs to extend the port more laterally to blend in the "smirk buckle" and nasolabial fold.

All in all, the volume of dermal filler collectively is approximately 25% more on the more contoured L side than on the heavier R side.

FIG. 22 illustrates an injection plan for an SS-G2 corrective solution for the lip and mouth area. In FIG. 22, the left column figures show the patient's lips and mouth area at rest, the right column of figures show the patient's lips and mouth area with animation. Most patients do not notice they have lip asymmetry at rest, let alone on animation. A goal of SSM for this area is to create more symmetry both at rest and animated. The lip and mouth ASSG scale align with the grade assignment, but the correction amounts are smaller than the face if you are only correcting the lips.

As can be observed in the photos before injection (2220-2223) and the injection plan (2222-2223), more product is needed in the upper and lower L lip to achieve balance because the entire L lip is thinner and more linear. The upper R lip curls under or involutes as the cheek above it is heavy and pushes it down. The lower R lip's shape does not need to be changed, just slightly filled to match the R lower lip post injection. As observable from the correction photos (2224-2225), the corrections make both sides more symmetrical and minimize the involution of the upper R lip. Generally, when addressing asymmetry caused by LOA position using SSM, the correction is slightly more on the L side. For example, in FIG. 22, the total correction performed in this area was 1 cc with 0.15 cc additional dermal filler injected on the L hemiface.

SSM specifies that, for SS-Lip-G1, approximately 10% more filler is needed on the L lip and mouth. For SS-Lip-G2, approximately 15% more filler is needed on the L lip and mouth. (For the counter positions due to ROA caused asymmetries, the sides are opposite.)

Symmetry Solutions Method of Treatment General Guidelines

In general, the Symmetry Solutions Method of Treatment plan is based upon carefully balancing a number of factors including cost of dermal filler injections and the desire to return a patient's facial features to a more youthful appearance, create contour or something interesting to observe, or to disguise too much contour, softening the face. Typically, the goal is to return a patient's facial features to their own individual baseline—often established using photos of a younger version of the patient and then injecting just a little more to create more contour since an observer's eye goes there first. During the SSM injection session(s), the injector makes adjustments to different zones based upon factors such as how the live tissue is responding (some tissue absorbs filler and changes faster than others); how the lifting, projecting, contouring, and blending is actually resulting, not wanting to overfill; individual patient desires (injecting towards a baseline and not necessarily towards a fully corrected vision). Even with these individual zone adjustments, the overarching principle of SSM is to inject the more contoured side more than the heavier side and within the ranges of 10-20% for an ASSG grade 1 (SS-G1) face and 21-30% for an ASSG grade 2 (SS-G2). Further, the SSM principles result in superior lifting, contouring procedure by administering 10% more filler to the light reflective area of the heavier side, and blending, softening, inferiorly, and equalizing the mid and lower face of the more contoured side to reduce the appearance of asymmetries.

Also, although certain terms are used primarily herein, other terms could be used interchangeably to yield equivalent embodiments and examples. In addition, terms may have alternate spellings which may or may not be explicitly mentioned, and all such variations of terms are intended to be included.

In this description, numerous specific details are set forth in order to provide a thorough understanding of the described techniques. The embodiments described also can be practiced without some of the specific details described herein, or with other specific details, such as changes with respect to the ordering of the logic, different logic, etc. Thus, the scope of the techniques and/or functions described are not limited by the particular order, selection, or decomposition of aspects described with reference to any particular routine, module, component, and the like.

All of the above U.S. patents, U.S. patent application publications, U.S. patent applications, foreign patents, foreign patent applications and non-patent publications referred to in this specification and/or listed in the Application Data Sheet are incorporated herein by reference, in their entireties.

From the foregoing it will be appreciated that, although specific embodiments have been described herein for purposes of illustration, various modifications may be made without deviating from the spirit and scope of the invention.

The invention claimed is:

1. A method for treating a patient with dermal filler injections to correct facial asymmetry using an asymmetry severity scale guide, wherein the patient suffers from asymmetrical facial features caused by fetal lie position during gestation, comprising:
   evaluating the face of the patient to determine whether the patient suffers from facial asymmetry caused by fetal lie position during gestation that is treatable in accordance with the asymmetry severity scale guide ("ASSG");
   when it is determined that the patient suffers from facial asymmetry caused by fetal lie position during gestation that is treatable in accordance with the ASSG,
      determining a severity grade of the facial asymmetry treatable in accordance with the asymmetry severity scale guide; and
      when it is determined that the severity grade of the facial asymmetry is a grade 1 asymmetry, treating the face of the patient with dermal injections with more filler volume applied to the more contoured hemi-face than to the heavier hemi-face; and
      when it is determined that the severity grade of the facial asymmetry is a grade 2 asymmetry, treating the face of the patient with dermal injections with more filler volume applied to the more contoured hemi-face than to the heavier hemi-face and with more filler volume applied to the more contoured hemi-face than would be applied if the severity grade of the facial asymmetry were determined to be a grade 1 asymmetry;
   wherein at least some of the dermal injections are delivered to the cheek rectangle and the cheek circle of at least one hemi-face of the patient.

2. The method of claim 1 wherein, when it is determined that the severity grade of the facial asymmetry is a grade 1 asymmetry, the treating the face of the patient with dermal injections with more filler volume applied to the more contoured hemi-face than to the heavier hemi-face further comprises:
   treating the face of the patient with dermal injections with 10-20% more filler volume applied to the more contoured hemi-face than to the heavier hemi-face.

3. The method of claim 1 wherein, when it is determined that the severity grade of the facial asymmetry is a grade 1 asymmetry, the treating the face of the patient with dermal injections with more filler volume applied to the more contoured hemi-face than to the heavier hemi-face further comprises:
   treating the face of the patient with dermal injections with approximately 15% more filler volume applied to the more contoured hemi-face than to the heavier hemi-face.

4. The method of claim 1 wherein, when it is determined that the severity grade of the facial asymmetry is a grade 2 asymmetry, the treating the face of the patient with dermal injections with more filler volume applied to the more contoured hemi-face than to the heavier hemi-face further comprises:
　　treating the face of the patient with dermal injections with 21-35% more filler volume applied to the more contoured hemi-face than to the heavier hemi-face.

5. The method of claim 1 wherein, when it is determined that the severity grade of the facial asymmetry is a grade 1 asymmetry, the treating the face of the patient with dermal injections with more filler volume applied to the more contoured hemi-face than to the heavier hemi-face further comprises:
　　treating the face of the patient with dermal injections with approximately 25% more filler volume applied to the more contoured hemi-face than to the heavier hemi-face.

6. The method of claim 1 wherein the amount of filler volume applied to the more contoured hemi-face than to the heavier hemi-face is determined at least in part dynamically by assessing an amount of filler required to return the face of the patient to a patient centric baseline associated with an earlier age of the patient.

7. The method of claim 1 further comprising:
　　adding more filler to the light reflective area of Zone 2 on the heavier hemi-face than on the light reflective area of Zone 2 on the more contoured hemi-face to add more contour to the heavier hemi-face.

8. The method of claim 1 wherein the evaluating the face of the patient to determine whether the patient suffers from facial asymmetry caused by fetal lie position during gestation that is treatable in accordance with the asymmetry severity scale guide further comprises:
　　obtaining measurements of facial features;
　　observing whether one side of the face appears heavier than an other side of the face and the other side of the face appears more contoured than the one side of the face and, when so, determining that the patient suffers from facial asymmetry; and
　　evaluating the patient that suffers from facial asymmetry to determine whether the patient has an associated birth deformity affecting asymmetry of the face of the patient;
　　when the patient has the associated birth deformity affecting asymmetry of the face of the patient, determining that the patient is not treatable in accordance with the asymmetry severity scale guide; and
　　when the patent does not have the associated birth deformity affecting asymmetry of the face of the patient, determining that the patient suffers from facial asymmetry caused by fetal lie position during gestation that is treatable in accordance with the asymmetry severity scale guide.

9. The method of claim 8 wherein the evaluating the patient that suffers from facial asymmetry to determine whether the patient has an associated birth deformity affecting asymmetry of the face of the patient is at least in part based upon answers of the patient to questions regarding history of the patient.

10. The method of claim 8 wherein the observing of whether one side of the face appears heavier than an other side of the face and the other side of the face appears more contoured than the one side of the face is assessed by comparing relative appearance of both cheeks of the patient, both sides of the mouth of the patient at rest and when smiling, and both nasolabial folds of the patient.

11. The method of claim 8 wherein the observing of whether one side of the face appears heavier than an other side of the face and the other side of the face appears more contoured than the one side of the face is assessed by observing that one side of the face in entirety is larger than the other side of the face.

12. The method of claim 1, further comprising:
　　when it is determined that the patient face suffers from fetal lie position caused asymmetry treatable in accordance with the asymmetry severity scale guide,
　　when the observed left side of the patient face is more contoured than the right side of the patient face and the right side of the patient face is heavier or larger than the left side of the patent face, characterizing the facial asymmetry treatable in accordance with the asymmetry severity scale guide as Left Occiput Anterior ("LOA") asymmetry; and
　　when the observed right side of the patient face is more contoured than the left side of the patient face and the left side of the patient face is heavier or larger than the right side of the patent face, characterizing the facial asymmetry treatable in accordance with the asymmetry severity scale guide as Right Occiput Anterior ("ROA") asymmetry.

13. The method of claim 12, further comprising:
　　when it is determined that the severity grade of the facial asymmetry is a grade 1 asymmetry,
　　when the facial asymmetry is characterized as LOA asymmetry, treating the left side of the face of the patient with dermal injections having 25% more filler volume than the right side of the face of the patient; and
　　when the facial asymmetry is characterized as ROA asymmetry, treating the right side of the face of the patient with dermal injections having 25% more filler volume than the left side of the face of the patient.

14. The method of claim 12, further comprising:
　　when it is determined that the severity grade of the facial asymmetry is a grade 2 asymmetry,
　　when the facial asymmetry is characterized as LOA asymmetry, treating the left side of the face of the patient with dermal injections having 33% more filler volume than the right side of the face of the patient; and
　　when the facial asymmetry is characterized as ROA asymmetry, treating the right side of the face of the patient with dermal injections having 33% more filler volume than the left side of the face of the patient.

15. The method of claim 1 wherein when the determining a severity grade of the facial asymmetry treatable in accordance with the asymmetry severity scale guide results in a severity grade that is neither grade 1 nor grade 2 asymmetry or is unclear, treating the face of the patient with dermal injections with 33% more filler volume on the more contoured hemi-face than the heavier hemi-face consistent with grade 2 asymmetry.

16. The method of claim 1 wherein the cheek rectangle of the at least one hemi-face of the patient extends medially 1.5-2 inches.

17. The method of claim 1 wherein the cheek circle of the at least one hemi-face of the patient has a diameter of 1.5-2 inches.

18. The method of claim 1, further comprising:
　　determining that the severity grade of the facial asymmetry is a grade 1 asymmetry when at least one of the following factors is observed:

the face of the patient is displays more contour than fat on both sides of the face of the patient; and/or a plurality of facial zones of the face of the patient reside in distinct planes.

19. The method of claim 1, further comprising:

determining that the severity grade of the facial asymmetry is a grade 1 asymmetry when at least one of the following factors is observed:

the face of the patient has a narrow and rectangular appearance; and/or both sides of the face of the patient appear flat and lack contour.

20. The method of claim 1, further comprising:

determining that the severity grade of the facial asymmetry is a grade 1 asymmetry when both sides of the face of the patient appear round and lack contour and it is difficult to observe bone structure of the face of the patient through adipose tissue.

21. The method of claim 1, further comprising:

applying injections of the dermal filler to one or more of six zones on each hemi-face of the patient according to the asymmetry severity scale guide, wherein the six zones include a temple and brow zone ("zone 1"), a medial and superior lateral cheek zone ("zone 2"), an inferior lateral cheek, preauricular fossa, and nasolabial fold zone ("zone 3"), a lips and superior oral commissure zone ("zone 4"), a chin and inferior oral commissure zone ("zone 5"), and a jawline zone ("zone 6").

22. The method of claim 21 wherein the application of the dermal filler injections is performed to a plurality of the six zones in a sequence of applying dermal filler to zone 3 after applying dermal filler to zone 2, applying dermal filler to zone 5 after applying dermal filler zone 2, zone 3, and zone 4; and applying dermal filler to zone 6 after applying dermal filler zone 5.

23. The method of claim 21 wherein the application of the dermal filler injections to zone 1, zone 2, and zone 4 can be applied in any sequence or as stand-alone applications of dermal filler to the face of the patient.

24. The method of claim 21 wherein the application of the dermal filler to the one or more of six zones on each hemi-face of the patient according to the asymmetry severity scale guide further comprises:

applying 2-3 cc of dermal filler to the temple and brow zone; and/or applying 2-4 cc of dermal filler to the medial and superior lateral cheek zone; and/or;

applying 3-5 cc of dermal filler to the inferior lateral cheek, preauricular fossa, and nasolabial fold zone; and/or applying 1-2 cc of dermal filler to the lips and superior oral commissure zone; and/or applying 3-6 cc of dermal filler to the chin and inferior oral commissure zone; and or applying 3-6 cc of dermal filler to the jawline zone.

25. The method of claim 24 wherein a total of all such applications of dermal filler are applied with 10-20% more filler volume applied to the more contoured hemi-face than to the heavier hemi-face when it is determined that the severity grade of the facial asymmetry is a grade 1 asymmetry.

26. The method of claim 25 wherein a total of all such applications of dermal filler are applied with 21-30% more filler volume applied to the more contoured hemi-face than to the heavier hemi-face when it is determined that the severity grade of the facial asymmetry is a grade 2 asymmetry.

* * * * *